US009018247B2

(12) United States Patent
Setchell et al.

(10) Patent No.: US 9,018,247 B2
(45) Date of Patent: *Apr. 28, 2015

(54) COMPOSITIONS AND PRODUCTS CONTAINING S-EQUOL, AND METHODS FOR THEIR MAKING

(75) Inventors: Kenneth David Reginald Setchell, Cincinnati, OH (US); Sidney John Cole, Port Macquarie (AU)

(73) Assignees: Children's Hospital Medical Center, Cincinnati, OH (US); Australian Health & Nutrition Association Limited, Berkeley Vale, New South Wales (AU)

(*) Notice: Subject to any disclaimer, the term of this patent is extended or adjusted under 35 U.S.C. 154(b) by 0 days.

This patent is subject to a terminal disclaimer.

(21) Appl. No.: 13/150,797

(22) Filed: Jun. 1, 2011

(65) Prior Publication Data

US 2012/0004189 A1 Jan. 5, 2012

Related U.S. Application Data

(63) Continuation of application No. 12/167,813, filed on Jul. 3, 2008, now Pat. No. 7,960,432, which is a continuation of application No. 10/625,934, filed on Jul. 24, 2003, now Pat. No. 7,396,855.

(60) Provisional application No. 60/398,270, filed on Jul. 24, 2002.

(51) Int. Cl.
| | | |
|---|---|---|
| A61K 31/353 | (2006.01) | |
| C07D 311/58 | (2006.01) | |
| A61K 31/352 | (2006.01) | |
| A23L 1/30 | (2006.01) | |
| A61K 8/49 | (2006.01) | |
| A61K 9/00 | (2006.01) | |
| A61Q 19/00 | (2006.01) | |
| C07D 311/74 | (2006.01) | |

(52) U.S. Cl.
CPC ............ *A61K 31/352* (2013.01); *C07D 311/58* (2013.01); *A23L 1/30* (2013.01); *A61K 8/498* (2013.01); *A61K 9/0014* (2013.01); *A61K 31/353* (2013.01); *A61K 2800/10* (2013.01); *A61Q 19/00* (2013.01); *C07D 311/74* (2013.01)

(58) Field of Classification Search
CPC ........................... A61K 31/353; C07D 311/58
USPC ......... 424/93.44; 514/456; 549/399, 408, 406
See application file for complete search history.

(56) References Cited

U.S. PATENT DOCUMENTS

| | | |
|---|---|---|
| 4,390,559 A | 6/1983 | Zilliken |
| 4,814,346 A | 3/1989 | Albert et al. |
| 5,141,746 A | 8/1992 | Fleury et al. |
| RE34,457 E | 11/1993 | Okamoto et al. |
| 5,352,384 A | 10/1994 | Shen |
| 5,424,331 A | 6/1995 | Shlyankevich |
| 5,498,631 A | 3/1996 | Gorbach et al. |
| 5,523,087 A | 6/1996 | Shlyankevich |
| 5,830,887 A | 11/1996 | Kelly |
| 5,726,034 A | 3/1998 | Bryan et al. |
| 5,733,926 A | 3/1998 | Gorbach |
| 5,804,234 A | 9/1998 | Suh et al. |
| 5,849,798 A | 12/1998 | Charpentier et al. |
| 5,855,892 A | 1/1999 | Potter et al. |
| 5,942,539 A | 8/1999 | Hughes, Jr. et al. |
| 5,952,374 A | 9/1999 | Clarkson, Jr. et al. |
| 5,958,946 A | 9/1999 | Styczynski et al. |
| 5,990,291 A | 11/1999 | Waggle et al. |
| 6,004,558 A | 12/1999 | Thurn et al. |
| 6,020,471 A | 2/2000 | Johns et al. |
| 6,054,636 A | 4/2000 | Fader |
| 6,060,070 A | 5/2000 | Gorbach |
| 6,083,526 A | 7/2000 | Gorbach |
| 6,146,668 A | 11/2000 | Kelly et al. |
| 6,159,959 A | 12/2000 | Miller |
| 6,194,450 B1 | 2/2001 | Charpentier et al. |

(Continued)

FOREIGN PATENT DOCUMENTS

| | | |
|---|---|---|
| EP | 1 025 850 A1 | 8/2000 |
| JP | H02-124883 | 5/1990 |

(Continued)

OTHER PUBLICATIONS

Muthyala, et al., Equol, a natural estrogenic metabolite from soy isoflavones: convenient preparation and resolution of R- and S-equols and their differing binding and biological activity through estrogen receptors alpha and beta, Bioorganic & Medicinal Chemistry, vol. 12, Iss. 6, 2004, pp. 1559-1567.*

Magee, et al., Equol: A Comparison of the Effects of the Racemic Compound With That of the Purified S-Enantiomer on the Growth, Invasion, and DNA Integrity of Breast and Prostate Cells In Vitro, Nutrition and Cancer, vol. 54, Iss. 2, 2006, pp. 232-242.*

Lamberton et al. (Aust. J. Chem., 1978, 31, 455-457, p. 455, line 15-16).*

Lamberton et al. (Aust. J. Chem., 1978, 31, 455-457).*

Widyarini et al. (Photochemistry and Photobiology, 2001, 74(3): 465-470).*

(Continued)

*Primary Examiner* — Robert Havlin
(74) *Attorney, Agent, or Firm* — Rothwell, Figg, Ernst & Manbeck, P.C.

(57) ABSTRACT

A composition for use in making commercial food and skin products comprising S-equol or mixtures, including both a non-racemic mixture and a racemic mixture, of S-equol and R-equol. The composition can be used to make articles of commerce such as food supplements, pharmaceuticals, and medicaments. The compositions are useful in a method of delivering S-equol to a mammal to prevent or treat a disease or associated condition, including hormone-dependent diseases or conditions such as cardiovascular disease, lipid disorder, osteopenia, osteoporosis, liver disease, and acute ovarian estrogen deficiency. The S-equol enantiomer can be produced in a biological synthesis from the metabolism of an isoflavone by an organism.

37 Claims, 7 Drawing Sheets

(56) References Cited

U.S. PATENT DOCUMENTS

| | | | |
|---|---|---|---|
| 6,242,594 | B1 | 6/2001 | Kelly |
| 6,258,856 | B1 | 7/2001 | Chamberlain et al. |
| 6,261,565 | B1 | 7/2001 | Empie et al. |
| 6,326,366 | B1 | 12/2001 | Potter et al. |
| 6,340,703 | B1 | 1/2002 | Kelly |
| 6,375,994 | B1 | 4/2002 | Paul et al. |
| 6,455,032 | B1 | 9/2002 | Kelly et al. |
| 6,497,906 | B1 | 12/2002 | Kelly |
| 6,509,043 | B1 | 1/2003 | Høie |
| 6,518,301 | B1 | 2/2003 | Barlaam et al. |
| 6,544,566 | B1 | 4/2003 | Waggle et al. |
| 6,562,380 | B1 | 5/2003 | Kelly |
| 6,565,864 | B2 | 5/2003 | Pillai et al. |
| 6,599,536 | B1 | 7/2003 | Kelly et al. |
| 6,638,543 | B2 | 10/2003 | Kang et al. |
| 6,642,212 | B1 | 11/2003 | Kelly |
| 6,649,648 | B1 | 11/2003 | Kelly et al. |
| 6,716,424 | B1 * | 4/2004 | Uchiyama et al. ......... 424/93.44 |
| 6,987,098 | B2 * | 1/2006 | Kelly .............................. 514/54 |
| 7,025,998 | B2 | 4/2006 | Senin et al. |
| 7,396,855 | B2 * | 7/2008 | Setchell et al. ................ 514/456 |
| 7,960,432 | B2 * | 6/2011 | Setchell et al. ................ 514/456 |
| 8,153,684 | B2 * | 4/2012 | Lephart et al. ................ 514/456 |
| 2002/0001565 | A1 | 1/2002 | Shapiro |
| 2002/0019377 | A1 | 2/2002 | Jenkins et al. |
| 2002/0035074 | A1 | 3/2002 | Kelly |
| 2002/0160064 | A1 | 10/2002 | Zulli et al. |
| 2002/0198248 | A1 | 12/2002 | Kelly et al. |
| 2003/0018060 | A1 | 1/2003 | Kelly et al. |
| 2003/0027772 | A1 | 2/2003 | Breton |
| 2003/0059384 | A1 | 3/2003 | Kelly et al. |
| 2003/0078214 | A1 | 4/2003 | Kelly |
| 2003/0219499 | A1 | 11/2003 | Kelly et al. |
| 2007/0043108 | A1 | 2/2007 | Lephart et al. |
| 2010/0076071 | A1 | 3/2010 | Lephart et al. |
| 2010/0087519 | A1 * | 4/2010 | Lephart et al. ................ 514/456 |

FOREIGN PATENT DOCUMENTS

| | | | |
|---|---|---|---|
| WO | WO 93/23069 | 11/1993 | |
| WO | WO 94/23716 | 10/1994 | |
| WO | WO 96/10341 | 4/1996 | |
| WO | WO 97/06273 | 2/1997 | |
| WO | WO 98/02194 | 5/1998 | |
| WO | 9826784 A1 | 6/1998 | |
| WO | 9850026 A1 | 11/1998 | |
| WO | WO 98/48790 | 11/1998 | |
| WO | 98/56373 A1 | 12/1998 | |
| WO | WO99/07392 * | 2/1999 | ............. A61K 35/74 |
| WO | 9949851 A1 | 10/1999 | |
| WO | 99/61028 A1 | 12/1999 | |
| WO | 00/13661 A1 | 3/2000 | |
| WO | 00/30663 A1 | 6/2000 | |
| WO | 00/41491 A2 | 7/2000 | |
| WO | 00/49009 A1 | 8/2000 | |
| WO | 00/62765 A2 | 10/2000 | |
| WO | 00/62774 A1 | 10/2000 | |
| WO | 02/03976 A1 | 1/2002 | |
| WO | 02/03977 A2 | 1/2002 | |
| WO | 02/03992 A2 | 1/2002 | |
| WO | WO 02/11675 | 2/2002 | |
| WO | 02/053108 A2 | 7/2002 | |
| WO | 02/062367 A1 | 8/2002 | |
| WO | WO 02/087517 | 11/2002 | |
| WO | WO 02/089757 | 11/2002 | |
| WO | WO 2004/022023 | 3/2004 | |
| WO | WO 2004/026274 | 4/2004 | |
| WO | WO 2004/039327 A2 | 5/2004 | |

OTHER PUBLICATIONS

Setchell et al. (Am. J. Clin. Nutr., 2005, 81:1072-9).*

Gimenez, I. et al., "Renal and Vascular Actions of Equol in the Rat," Journal of Hypertension, 1997, vol. 15, No. 11, pp. 1303-1308.

Pereboom, D. et al., "Antioxidant Intracellular Activity of Genistein and Equol," Journal of Medicinal Food, 1999, vol. 2, Nos. 3-4, pp. 253-256.

Bannwart, C. et al., "Identification of the Phyto-oestrogen 3',7-Dihydroxyisoflavan, an Isomer of Equol, in Human Urine and Cow's Milk," Biomedical and Environmental Mass Spectrometry, 1988, vol. 17, pp. 1-6.

Wiseman, H., "The Therapeutic Potential of Phytoestrogens," Expert Opinion on Investigational Drugs, 2000, vol. 9, No. 8, pp. 1829-1840.

Lou, J.M. et al., "Natriuretic Effect of Equol," Journal of Medicinal Food, 1999, vol. 2, Nos. 3-4, pp. 257-260.

Lephart, E.D., "Dietary Soy Phytoestrogen Effects on Brain Structure and Aromatase in Long-Evans Rats," Neuroreport, 2001, vol. 12, No. 16, pp. 3451-3455.

Chin-Dusting, Jaye P,F., et al, "The Vascular Activity of Some Isoflavone Metabolites: Implications for a Cardioprotective Role," British Journal of Pharmacology, 2001, vol. 133, pp, 595-605.

Axelson, M., et al., "Soya—A Dietary Source of the Non-Steroidal Oestrogen Equol in Man and Animals," Journal of Endocrinology, 1984, vol. 102, pp. 49-56.

Brown, N.M. et al., "The Chemopreventive Action of Equol Enantiomers in a Chemically-Induced Animal Model of Breast Cancer," Carcinogenesis Advance Access published Jan. 28, 2010, © The Author 2010, published by Oxford University Press, 35 pages.

Welshons, W.V., et al., "Stimulation of breast cancer cells in vitro by the environmental estrogen enterolactone and the phytoestrogen equol," Breast Cancer Research and Treatment, 10: pp. 169-175, 1987, copyright Martinus Nijhoff Publishers, Boston.

Jaonnou et al., J. Steroid, Biochem. Molec. Biol., 54, 167-184.

Marrian,G.F. et al., "CXLV, Equol, A New Inactive Phenol Isolated From the Ketohydroxy-Oestrin Fraction of Mares' Urine," Journal of Biochemistry, 1932, pp. 1227-1232.

Marrian, G.F., et al., "CXC. The Constitution of Equol," Journal of Biochemistry, 1935, pp. 1586-1589.

Gimenez et al., "Renal and Vascular Actions of Equol in the Rat," Journal of Hypertension, 1997, Nov. 15(11): pp. 1303-1308 (Abstract).

Pereboom, D., "Antioxidant Intracellular Activity of Genistein and Equol," Journal of Medicinal Food, 1999, vol. 2, pp. 253-266 (Abstract).

Papers filed in U.S. Appl. No. 11/059,951, "Use of Equol for Treating Skin Diseases," filed Feb. 17, 2005, Edwin D, Lephart et al., 78 pages.

Widyarini, S, et al., "Isoflavonoid Compounds from Red Clover (Trifolium pratense) Protect from Inflammation and Immune Suppression Induced by UV Radiation," Photochemistry and Photobiology, vol. 74, No. 3, pp. 465-470, Dec. 2001.

Adlercreutz, H., et al., Excretion of The Lignans Enterolactone and Enterodiol and of Equol in Omnivorous and Vegetarian Postmenopausal Women and in Women with Breast Cancer. The Lancet, Dec. 11, 1982, 1295-1299.

Akaza, H., et al,, Is Daidzein Non-metabolizer High Risk for Prostate Cancer? A case-controlled Study of Serum Soybean Isoflavone Concentration. Jpn J Clin Oncol, 2002, 32(8): 296-300.

Ingram, D., et al., Case-control study of phyto-oestrogens and breast cancer. The Lancet, Oct. 4, 1997, vol. 350, 990-994.

Kostelac, D., et al., Phytoestrogens Mmodulate Binding Response of Estrogen Receptors α and β to the Estrogen Response Element. Journal of Agricultural and Food Chemistry, 2003, 51(26): 7632. 7635.

Lephart, E., Antiaging Effects of Equol: A Unique Antiandrogenic Isoflavone Metabolite and its Influence in Stimulating Collagen Deposition in Human Dermal Monolayer Fibroblasts, J Am Acad Dermatol, Mar. 2006, AB103.

Lephart, E.D., Equol; A unique anti-androgenic isofavone metabolite stimulates Collagen (I and III), elastin and human fibroblast proliferation and inhibits matrix metalloproteinases and elastase in 3D cultures via FACS analysis, J Am Acad Dermatol, Mar. 2005, 85.

Lund, T.D., Altered sexually dimorphic nucleus of the preoptic area (SDN-POA) volume in adult Long-Evans rats by dietary soy phytoestrogens; Brain Research, 2001, 914(1-2).

(56) References Cited

OTHER PUBLICATIONS

Setchell, D.R., et al., S-Equol, a potent ligand for estrogen receptor β, is the exclusive enantiomeric form of the soy lsofavone metabolite produced by human intestinal bacterial flora, *The American Journal of Clinical Nutrition*, May 2005, 81, 1072-1079.
Weber, K.S., Dietary Soy-phytoestrogens decrease testosterone levels and prostate weight without altering LH, prostate 5α-reductase or testicular steroidogenic acute regulatory peptide levels in adult male Sprague-Dawley rats, *Journal of Endocrinology*, 2001, 170:591-599.
Office Action dated Mar. 27, 2007 from related U.S. Appl. No. 10/625,989.
Alda, J. et al., Purification and Chemical Characterization of a Potent Inhibitor of the Na—K—CI Cotransport System in Rat Urine, *Biochemical and Biophysical Research Communications* (1996), vol. 221, pp. 279-285.
Merck Index, 1996, 12th Edition, p. 3677.
Luk et al., J. Natural Products, 46(6), 852-861, especially p. 853.
LC Laboratories and US Biological product list.
Kinjo, J., Phytoestrogens. Japanese Journal of Clinical Medicine, Dec. 2000, 58(12), pp. 2434-2438.
Lund, TD et al., Equol is a Novel Anti-Androgen that Inhibits Prostate Growth and Hormone Feedback, Biol. Reprod., Apr. 2004; 70(4) 1188-95, E-Pub. Dec. 17, 2003.
Atkinson, C. et al, In Vitro Incubation of Human Feces with Daidzein and Antibiotics Suggests Interindividual Differences in the Bacteria Responsible for Equol Production, Amer. Society for Nutritional Sciences, 134:596-599, Mar. 2004.
Setchell, Kenneth, D.R.. et al. Phytoestrogens: The Biochemistry, Physiology, and Implications for Human Health of Soy Isoflavones, Am J. Clin Nutri 1998, pp. 1333S-1346S.
Aldercreutz, H. et al, Determination of Urinary Lignans And Phytoestrogen Metabolites, Potential Antiestrogen and Anticarcirtogens in Urine of Women on Various Habitual Diets, J. Steroid Biochem, vol. 25, pp. 791-797 (1996).
Thompson, M.A. et al., Characterization of the Estrogenic Properties of A Nonsteroidal Estrogen, Equol, Extracted from Urine of Pregnant Macaques Biol Reprod, Nov. 1984; 31: 705-713.
Hedlund, T.E. et al., Soy Isoflavonoid Equol Modulates the Growth of Benign and Malignant Prostatic Epithelial Cells in Vitro, The Prostate 54;68-78 (2003) accepted May 14, 2002.
Duncan, A. M. et al., Premenopausal Equol Excretors Show Plasma Hormone Profiles Associated with Lowered Risk of Breast Cancer, Cancer Epidemiol, Biomarkers Prev vol. 9: 581-586. Jun. 2000.
Hwang, J. et al., The Phytoestrogen Equol Increases Nitric Oxide Availability by Inhibiting Superoxide Production: An Antioxidant Mechanism for Cell-Mediated LDL Modification, Free Radical Biology & Medicine, vol. 34, No. 10, pp. 1271-1282, (2003).
Muthyala, R. S., Equol, a Natural Estrogenic Metabolite from Soy Isofavones: Convenient Preparation and Resolution of R- and S-Equols and Their Differing Binding and Biological Activity Through Estrogen Receptors Alpha and Beta, Bioorganic & Medicinal Chemistry 12 pp. 1559-1567 (2004), accepted Nov. 19, 2003.
Sathyamoorthy, N. et al., Differential Effects of Dietary, Phytooestrogens Daidzein and Equol on Human Breast Cancer MCF-7 Cells, European Journal of Cancer, vol. 33, Issue 14, Dec. 1997, pp. 2384-2389.
Ogawara, H., A specific Inhibitor for Tyronsine Protein Kinase from Pseudomonas, The Journal of Antibiotics, vol. 39(4), Apr. 1936, 606-608.
U.S. Appl. No. 10/625,989, filed Jul. 24, 2003, Setchell, et al.
U.S. Appl. No. 10/533,045, filed Apr. 28, 2005, Lephart, et al.
U.S. Appl. No. 11/059,951, filed Feb. 17, 2005, Lephart, et al.
Setchell, Kenneth D.R. et al., "Bioavailability of Pure isoflavones In Healthy Humans and Analysis of Commercial Soy Isoflavone Supplements," American Society for Nutritional Sciences, 2001, pp. 1362S-1375S.
Brown, Nadine M. et al., "Animal Models Impacted by Phytoestrogens in Commercial Chow; Implications for Pathways Influenced by Hormones," Laboratory Investigation, May 2001, vol. 81, No. 5, pp. 735-747.

Lamberton et al., Aust. J. Chem., 1978, 31, 455-457, especially p. 457, Experimental (b), last sentence.
Wähälä, Kristiina et al., "Synthesis of the [2H]—Labelled Urinary Lignans, Enterolactone and Enterodiol, and the Phytoestrogen Daidzein and its Metabolites Equol and O-Demethyl-angolensin," J. Chem. Soc, Perkin Trans. I 1986, pp. 95-98.
Kohli, J.C. et al., "Specific separation of equol from estrogens by thin-layer chromatography," Journal of Chromatography, 129 (1976), pp. 473-474, Elsevier Scientific Publ. Co., Amsterdam.
Setchell et al., Am. J. Clin. Nutr., 2002, 76, 447-453, especially p. 447, col. 2, approximately lines 20-21.
Atsutane, Ohta et al., "A combination of Dietary Fructooligosaccharides and Isoflavone Conjugates Increases Femoral Bone Mineral Density and equol Production in Ovariectomized Mice," American Society for Nutritional Sciences, 2002, pp. 2048-2054.
Setchell, K.D.R. et al., "Nonsteroidal estrogens of dietary origin; possible roles in hormone-dependent disease," The American Journal of Clinical Nutrition 40, Sep. 1984, pp. 569-578.
Alvira, E. et al., "Molecular modeling study for chiral separation of equol enantiomers by β-cyclodextrin," Chemical Physics 240 (1999), pp. 101-108, Elsevier Science B.V.
Anderson, Edith L. et al., "The Identification of Equol as 7-Hydroxy-3-(4'-Hydroxyphenyl) Chroman, and the Synthesis of Racemic Equol Methyl Ether," J. Biol. Chem. 127:649-56 (1930).
Chiralcel® OD. Instruction Sheet, Daicel Chemical Industries, Ltd., Japan, May 1, 1995.
Chiralcel® OD. Instruction Sheet, Daicel Chemical Industries, Ltd., Exton, PA, Dec. 6, 1994.
Setchell, K.D.R. et al., "Dietary Phytoestrogens and Their Effect on Bone: Evidence from In Vitro and In Vivo, Human Observational, and Dietary Intervention Studies," Am. J. Clin. Nutr., 2003; 78 (suppl.): 593S-609S.
Sigma-Aldrich webpage. Equol, Product No. 45405, Jul. 10, 2003.
Sigma-Aldrich webpage, (±)-Equol Product No. 45405, Oct. 23, 2003.
Bowey, E. et al., "Metabolism of Isoflavones and Lignans by the Gut Microflora: a Study in Germ-Free and Human Flora Associated Rats," Food Chem. Toxicol., May 2003, 41 (5):631-6, Abstract only.
Rafii, F. et al., Variations in Metabolism of the Soy Isoflavonoid Daidzen by Human Intestinal Microfloras from Different Individuals, Arch, Microbiol., Jul. 2003; 180(1): 11:6, Epub May 29, 2003, Abstract only.
Widyarini, S. et al., "Isoflavonoid Compounds from Red Clover (*Trifolium pratense*) Protect from Inflammation and Immune Suppression Induced by UV Radiation," Photochem Photobiol, Sep. 2001; 74(3): 465-70, Abstract only.
Rowland, I.R. et al., "Interindividual Variation in Metabolism of Soy Isoflavones and Lignans: Influence of Habitual Diet on Equol Production by the Gut Microflora," Nutr. Cancer, 2000; 36(1): 27-32, Abstract only.
Kaziro, R. et al., "The Oestrogenicity of Equol in Sheep," J. Endocrinol., Dec. 1984; 103(3): 395-9, Abstract only.
Setchell, K.D.R. et al., "Bioavailability, Disposition, and Dose-Response Effects of Soy Isoflavones When Consumed by Healthy Women at Physiologically Typical Dietary Intakes," American Society for Nutritional Sciences, 2003, pp. 1027-1035.
Setchell, K.D.R. et al., "The Clinical Importance of the Metabolite Equol—A Clue to the Effectiveness of Soy and Its Isoflavones," American Society for Nutritional Sciences, 2002, pp. 3577-3584.
Axelson, M. et al., "The Identification of the Weak Oestrogen Equol [7-hydroxy-3-(4'-hydroxyphenyl)chroman] in Human Urine," Biochem. J., 1982, 201, 353-357. Printed in Great Britain.
Setchell et al., U.S. Appl. No. 10/625,989, filed Jul. 24, 2003.
Shelnutt et al., Am. J. Clin. Nutr., 2002, 76, 588-594, especially p. 588, col. 2, approximately lines 15 and 16.
Supplementary European Search Report dated Aug. 16, 2006, Appln. No. EP 03 76 5987.
Axelson (1984) "Soya—a dietary source of the non-steroidal oestrogen equol in man and animals," J. Endocr. 102:49-56.
Bannwart, et al. (1998) "Identification of the Phyto-oestrogen 3',7-Dihydroxyisoflavan, an Isomer of Equol, in Human Urine and Cow's milk," Biomedical and Environmental Mass Spectrometry, 17;1-6.

(56) References Cited

OTHER PUBLICATIONS

Jaonnou, et al. (1995) A Urinary Profile Study of Dietary Phytoestrogens. The Identification and Mode of Metabolism of New Isoflavonoids, J. Steroid Biochem. Molec. Biol. 54:167-184.

Kurosawa, et al. (1968) "The Absolute Configurations of the Animal Metabolite, Equol, Three Natrually Occurring Isoflavans, and One Natrual Isoflavanquinone," J. Chem. Soc. Chemical Communications 1265-67.

Luk, et al. (1983) "Isolation and Identification of 'Diazepam-Like' Compounds from Bovine Urine," J. Natural Products, 46(6), 852-861.

Merriam-Webster's Collegiate Dictionary (11th ed.) (2003). New York, NY: Merriam-Webster, Inc.

Ollis (1962) "Chapter 12 The Isoflavonoids," In T.A. Geissman (Ed.), The Chemistry of Flavonoid Compounds, pp. 353-405, New York: NY:MacMillan Company.

Setchell, et al. (2005) "S-Equol, a potent ligand for estrogen receptor $\beta$, is the exclusive enantiomeric form of the soy isoflavone metabolite produced by human intestinal bacterial flora," Am. J. Clin. Nut. 81:1072-79.

Wade, et al. (1994) "Handbook of Pharmaceutical Excipients," 2d Ed.

Widyarini, et al. (2001) "Isoflavonoid Compounds from Red Clover (*Trifolium pratense*) Protect from Inflammation and Immune Suppression Induced by UV Radiation," Photochemistry & Photobioiogy, 74:465-70.

Morito, K., et al., "Interaction of Phytoestrogens with Estrogen Receptors $\alpha$ and $\beta$," Biol. Pharm. Bull, 24(4):351-356 (2001).

Canadian Office Acton in Canadian Application Serial No. 2,492,754 dated Dec. 3, 2013, 8 pages.

Office Action issued in Canadian Patent Application No. 2,492,754, 7 pages (Sep. 5, 2014).

Database CA, Chemical Abstracts Service, XP002725673, Database accession No. 2002:227050, Mar. 26, 2002.

\* cited by examiner

COMPOSITIONS AND PRODUCTS CONTAINING S-EQUOL, AND METHODS FOR THEIR MAKING

CROSS-REFERENCE TO RELATED APPLICATIONS

This application is a continuation of U.S. application Ser. No. 12/167,813, filed Jul. 3, 2008, now U.S. Pat. No. 7,960,432, which in turn is a continuation of U.S. application Ser. No. 10/625,934, filed Jul. 24, 2003, now U.S. Pat. No. 7,396,855, which issued on Jul. 8, 2008, and claims benefit of U.S. Provisional Application No. 60/398,270, filed Jul. 24, 2002. The disclosures of all of the above applications are hereby incorporated by reference in their entireties.

BACKGROUND OF THE INVENTION

The nutritional value of soybeans and foods made of purified soy proteins is well established and the renaissance of interest in soy foods is largely the result of documented research of the potential health benefits of isoflavones, a class of phytoestrogens found in abundance in soybeans. Although the recent FDA approval allowing manufacturers of soy foods to make a heart health claim for soy foods containing the mandatory 6.25 g/serving of soy protein (FDA, 1999) did not recognize the value of soy's constituent isoflavones, studies now indicate that phytoestrogens contribute to the cholesterol-lowering effect while also having important non-steroidal properties that contribute to reduced cardiovascular risk factors. The low incidence of hormone-dependent diseases in Asian countries where soy is consumed regularly has been suggested to be due in part to the actions of soy isoflavones.

Phytoestrogens, particularly the isoflavones derived from soy, clover and kudzu, such as genistein, daidzein, glycitein, peurarin, and their glycosidic derivatives, biochanin A and formononetin, and their glycosidic derivatives, exhibit estrogenic properties in some mammalian and human tissues, and exhibit anti-estrogenic properties in other tissues by competitively inhibiting estrogen binding at estrogen receptor sites. Unlike estrogens, these isoflavone phytoestrogens seem not to be associated with an increased risk of breast and uterine cancers, and may actually inhibit the development of breast and prostate cancers.

Cardiovascular disease is a leading cause of morbidity and mortality, particularly in the United States and in Western European countries. Several causative factors are implicated in the development of cardiovascular disease including hereditary predisposition to the disease, gender, lifestyle factors such as smoking and diet, age, hypertension, and hyperlipidemia, including hypercholesterolemia. Several of these factors, particularly hyperlipidemia and hypercholesterolemia, contribute to the development of atherosclerosis, a primary cause of vascular and heart disease.

A high blood cholesterol concentration is one of the key risk factors for vascular disease and coronary heart disease in humans. Elevated low density lipoprotein cholesterol (hereafter "LDL-cholesterol") and total cholesterol are directly related to an increased risk of coronary heart disease [Cholesterol and Mortality: 30 Years of Follow-Up from the Framingham Study, Anderson, Castelli, & Levy, JAMA, Vol. 257, pp. 2176-80 (1987)] while a a low level of high density lipoprotein cholesterol (hereafter "HDL-cholesterol") is also a predisposing factor. Several clinical trials support a protective role of HDL-cholesterol against atherosclerosis. A study has shown that for every 1-mg/dL increase in HDL-cholesterol in the blood, the risk for coronary vascular disease is decreased by 3% in women [High-density Lipoprotein Cholesterol and Cardiovascular Disease: Four Prospective American Studies, Gordon, Probstfield, and Garrison et al., Circulation, Vol. 79, pp. 8-15 (1989)].

Estrogens play an important role in regulating lipid metabolism and maintaining healthy blood vessels, as evidenced by the escalation in plasma cholesterol that occurs after menopause and the fact that cardiovascular disease kills more women than men in the USA and most Western countries. For this reason, there has been a long held belief that HRT would benefit postmenopausal women by providing protection against CVD. The recent findings from the Women's Health Initiative Study of over 16,608 postmenopausal women taking HRT over an eight-year period has failed to show such benefits, and actually found an increased risk of death from thromboembolism and heart disease, especially in the first year of taking combined estrogen and progestin regimen, while significantly increasing the risk of breast cancer. As a consequence of these reports, HRT use has plummeted and women are now increasingly seeking alternative forms of estrogen to provide the benefits of postmenopausal estrogen deficiency. Phytoestrogens, such as isoflavones that act as natural selective estrogen receptor modulators by virtue of the conformational binding to the estrogen receptor are potential attractive alternatives and while there has been much published on the use of soy or clover isoflavones, there is a paucity of data on the potential value of the important metabolite, equol.

Recent studies have determined that soy isoflavones play a role in lowering blood concentrations of total cholesterol and LDL-cholesterol in animals, inhibiting the development of atherosclerosis. The effect of isoflavones on blood cholesterol levels in humans is more controversial, but several studies now show the need to have isoflavones present in soy protein to observe cholesterol-lowering effects. A key study by Crouse et al, showed a dose-dependent relationship between the reduction in serum total and LDL-cholesterol and the amount of isoflavones present in soy protein. Independent of the effects isoflavones may have on cholesterol homeostasis, there is now evidence that isoflavones exert important effects on blood vessels. Studies have shown reductions in lipid peroxidation, improvements in arterial reactivity, blood flow, and blood pressure, and decreases in platelet aggregation. We have recently found that a daily diet containing isoflavones reduced the level of C-reactive protein, which is one of the key markers of inflammation, and considered one of the precipitating factors in cardiovascular disease. All of the above are crucial risk-reduction factors for cardiovascular disease.

Isoflavones have been shown to have bone-sparing effects. Thus far 17 in vitro studies of cultured bone cells, 24 in vivo studies of animal models of postmenopausal osteoporosis, and 17 dietary intervention studies show that isoflavones have bone-sparing effects. In all of these studies it has been the soy isoflavones or clover isoflavones that have been examined. We have shown for the first time that equol is an important bone-trophic agent and that unlike estrogens, it has the ability to not only reduce the activity of the bone-resorbing cells, but can actually increase bone mineral density in postmenopausal women.

While the bulk of the scientific literature has focused on the natural isoflavones in soy or clover, little has been reported on the actions or effects of their intestinally derived metabolites and there remains a need to develop further compounds and methods that can safely provide treatment or preventive benefits in mammals and humans.

Equol (7-hydroxy-3-(4'-hydroxyphenyl)-chroman), a nonsteroidal estrogen, was first isolated and identified from pregnant mares urine in 1932 and was later identified in the urine of humans consuming soy food. Equol has a structure similar to the steroidal estrogen estradiol. Equol is unique among the isoflavones in that it possesses a chiral center and as such exists as two distinct enantiomeric forms, the R- and S-enantiomers. All previous studies on equol appear to have been conducted with the racemic form of equol. There has in general been a lack of appreciation that two forms of equol exist and to our knowledge no previous study has reported on the specific actions or activity of the individual enantiomers. Equol when originally identified in mare's urine was reported to be optically active, existing as the R-enantiomer. Later, this was found to be an incorrect assignment and evidence was provided that the form of equol isolated from horse urine was in fact the S-enantiomer. For the first time, we have evidence that the human form of equol produced in the intestine, is exclusively the S-enantiomer, and we have synthesized and isolated the individual enantiomers, and shown significant differences in their respective affinities for estrogens receptors (ER), ERα and ERβ.

While equol was originally found to have no estrogenic action when injected into ovariectomized mice in large doses, later findings showed that it was the agent responsible for an infertility syndrome in sheep.

Also, (−)equol was originally reported as having no estrogenic activity in the ovariectomized mouse, but later the racemic mixture of equol proved to behave as a weak estrogen, while its precursors, daidzein and formononetin had no or negligible estrogenic activity.

Equol is not normally present in the urine of most healthy adults unless soy is consumed. The formation of equol in vivo has been exclusively dependent on intestinal microflora as evidenced from the finding that germ-free animals do not excrete equol, and that equol is not found in the plasma and urine of newborn infants fed exclusively soy foods from birth.

Equol is exclusively a non-steroidal estrogen that does not occur naturally in any plant-based products.

BRIEF SUMMARY OF THE INVENTION

The present invention relates to a composition for use in making commercial products, comprising S-equol.

The invention further relates to an article of commerce comprising a non-racemic mixture of S-equol and R-equol.

The invention further relates to a food composition comprising an additive component comprising S-equol.

The invention further relates to a composition for topical application to skin, comprising S-equol and a vehicle.

The invention further relates to a method of making a composition comprising S-equol, comprising the steps of: 1) providing a first composition comprising an isoflavone capable of being converted to S-equol; 2) culturing the first composition with an organism capable of converting the isoflavone to S-equol; and 3) incubating the cultured composition for a time sufficient to convert a portion of the isoflavone to S-equol.

The invention additionally relates to a method of making a composition comprising S-equol, comprising the steps of: 1) providing a first composition comprising an isoflavone capable of being converted to S-equol; 2) combining the first composition with an enzyme selected from the group consisting of: an enzyme that is extracted from a bacterium capable of converting the isoflavone to S-equol, an alpha-glucosidase, a beta-glucosidase, beta-galactosidase, gluco-amylase, and pectinase, and a mixture thereof; and 3) incubating the combined composition for a time sufficient to convert a portion of the isoflavone to S-equol.

The invention also relates to a method of making S-equol product, comprising the steps of: 1) providing a composition comprising an equol enantiomer consisting essentially of S-equol, the composition being produced in a biological synthesis from the metabolism of an isoflavone by an organism; 2) extracting S-equol from the composition to form an product comprising S-equol, by an extraction selected from: a) a solvent extraction, comprising mixing the composition with a low molecular weight alcohol to provide an alcohol to water ratio of at least 40:60 and no more than 95:5, and b) an aqueous acid extraction, comprising mixing the composition at a pH of between about 4.0 and about 5.5; 3) concentrating the extract to a solids content of about 15% to about 55%; 4) diluting the concentrate to a solids content of about 6% to about 15%; and 5) separating a solid precipitate from the diluted solution; thereby forming the S-equol product.

The invention also relates to a method of delivering S-equol to a mammal to prevent or treat a disease or associated condition, comprising administering to the mammal a composition comprising S-equol or a conjugated analog thereof.

DETAILED DESCRIPTION OF THE INVENTION

Figure 1:
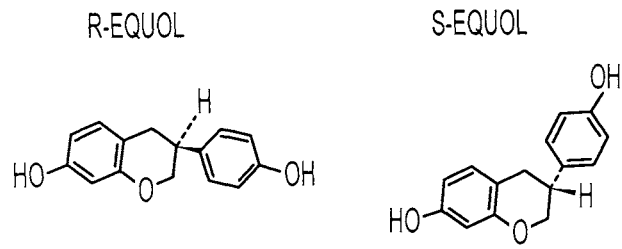
FIG. 1 shows the chemical structures of R-equol and S-equol enantiomers.

Equol is distinct from most isoflavones in having a chiral center due to the lack of a double bond in the heterocyclic ring. The phytoestrogen isoflavones from soy, daidzein, glycitein and genistein, from clover, formononetin and biochanin A, and from kudzu, peurarin, do not have a chiral center. FIG. 1 shows the chemical structures of R-equol and S-equol.

The R-equol and S-equol enantiomers conformationally differ and this is predicted to influence how equol fits into the binding site in the cavity of the dimerized ER complex. Many different in vitro assay systems have been employed to compare the estrogenicity of isoflavones. Independent of the assay system used, data for the relative molar binding affinities of equal, daidzein, and estradiol to uterine cytosolic receptors are 0.4, 0.1, and 1.0, respectively. These data however predate the recognition of distinct ER sub-types and the discovery of ERβ and therefore the relative binding affinities reflect affinities toward ERα as this is the predominant receptor in the uterus and take no account of the possible structure-activity differences in the enantiomeric forms of equol Several phytoestrogens, including equol, are unique among many estrogen-like substances for their preferential binding to ERβ protein and this may serve to explain some of the beneficial effects of soy isoflavones in tissue expressing this receptor sub-type, like the bone, brain and vascular endothelium. More recently, the binding affinity of equol for human ERα and ERβ was compared with several other isoflavones. The binding of equol to both receptors was similar to that of genistein, but equol induced transcription in gene expression more strongly than any other isoflavone, especially with ERα. Interestingly, daidzein in these in vitro systems shows poor affinity and transcriptional activity.

Approximately 50% of equol circulates in the free or unbound form, and this is considerably greater than the proportion of free daidzein (18.7%) or estradiol (4.6%) in plasma. Since it is the unbound fraction that is available for receptor occupancy this would effectively contribute to enhancing the overall potency of equol. Furthermore, R-equol and S-equol both possess unique antiandrogen properties by their ability to antagonize dihydrotestosterone in vitro and in vivo, thus expanding the potential therapeutic role of R-equol as a potential pharmacological agent in androgen related diseases. R-equol, we predict may also serve as a ligand for ERβ2 a novel estrogen receptor that may play a role in regulating expression of estrogen receptors ERα and ERβ and in this regard may prove to be a potential pharmacologic agent for the treatment or prevention of breast cancer and related hormonal conditions involving signaling pathways mediated through these receptors. R-equol also has antioxidant activity. So while R-equol is not physiological produced in the gastrointestinal tract in response to isoflavone ingestion, it is a unique isoflavone hitherto not recognized as, and that potentially is, an important pharmacological agent.

As shown in the Experiments section, it was determined that the S-enantiomer of equol is exclusively found in the urine and plasma of "equol-producing" adults consuming soy foods. This suggested that bacterial production of equol is probably enantiomeric-specific in the intestine, and, as shown in experiment (d) of the Experiments section, S-equol is the only equol enantiomer made by human intestinal bacteria cultured in vitro.

Compositions Containing S-Equol

A composition of the present invention comprises S-equol, and typically consists essentially of S-equol. The composition is used in making commercial and institutional products. The composition, or a product made therefrom, can be consumed orally or applied topically.

The product typically comprises a marketed or instinctional food product, a pharmaceutical, an OTC medicament, an ointment, liquid, cream or other material suitable for topical application. A food composition can comprise at least 1 mg, and up to 200 mg, S-equol per serving. An orally-administered medicament can comprise at least 1 mg, and up to 200 mg, S-equol per dose.

A product for topical application can comprise at least 0.1%, and up to 10%, by weight S-equol. A topical composition of the present invention can include other cosmetic and pharmaceutical actives and excipients. Such suitable cosmetic and pharmaceutical agents include, but are not limited to, antifungals, vitamins, anti-inflammatory agents, antimicrobials, analgesics, nitric oxide synthase inhibitors, insect repellents, self-tanning agents, surfactants, moisturizers, stabilizers, preservatives, antiseptics, thickeners, lubricants, humectants, chelating agents, skin penetration enhancers, emollients, fragrances and colorants.

The S-equol can also be an equol conjugate, conjugated at the C-4' or the C-7 position with a conjugate selected from the group consisting of glucuronide, sulfate, acetate, propionate, glucoside, acetyl-glucoside, malonyl-glucoside, and mixtures thereof.

A composition or preparation administered to subjects for the treating and/or prevention of, or for reducing the predisposition to, diseases and conditions related thereto can also comprises one or more pharmaceutically acceptable adjuvants, carriers and/or excipients. Pharmaceutically acceptable adjuvants, carriers and/or excipients are well known in the art, for example as described in the Handbook of Pharmaceutical Excipients, second edition, American Pharmaceutical Association, 1994 (incorporated herein by reference). S-equol can be administered in the form of tablets, capsules, powders for reconstitution, syrups, food (such as food bars, biscuits, snack foods and other standard food forms well known in the art), or in drink formulations. Drinks can contain flavoring, buffers and the like.

A composition of the invention can include one suitable for oral, rectal, optical, buccal (for example sublingual), parenteral (for example subcutaneous, intramuscular, intradermal and intravenous) and transdermal administration. The most suitable route in any given case will depend on the nature and severity of the condition being treated and the state of the patient.

The invention also includes articles of commerce comprising a composition that comprises a non-racemic mixture of equol, and typically comprises equol consisting essentially of S-equol. The article of commerce can be a food, including a beverage, and a health or personal care product.

The composition can typically be made by isolating the S-equol enantiomer from a racemic mixture of R-equol and S-equol (also referred to as (±)equol). Typically, the racemic mixture is a synthetic racemic mixture made by a synthetic route, such as the one described herein. Typically, the S-equol composition has an enantiomeric purity of 90% minimum enantiomeric excess ("EE") of S-equol. Typically, more purified compositions can be prepared having an EE of 96% minimum, and even more typically 98% minimum, of S-equol.

The composition of the invention can also comprise a non-racemic mixture of S-equol and R-equol, having an EE for S-equol of more than 0% and less than 90%. A composition that has an EE of 0% is a 50:50 racemic mixture of the two enantiomers. The composition can be made directly from a racemic mixture, by an incomplete separation and removal of R-equol enantiomer from the racemic mixture. The composition can also be made by combining a first equol component comprising a mixture of equol enantiomers, including both a non-racemic mixture and a racemic mixture of equol, with a second component comprising a composition consisting essentially of S-equol. This produces a non-racemic composition that has an excess of S-equol. Conversely, a non-racemic mixture can be prepared with an excess of R-equol enantiomer, by combining a first equol component comprising a mixture of equol enantiomers, including both a non-racemic mixture and a racemic mixture of equol, with a second component comprising a composition consisting essentially of R-equol. Depending upon the specific benefit or indication for the R-equol component and the S-equol component in a composition, a composition can be prepared comprising S-equol and R-equol at a ratio of S-equol to R-equol from greater than about 50:50 to about 99.5:1, more typically about 51:49 to about 99:1, and from less than about 50:50 to about 1:99.5, more typically about 49:51 to about 1:99.

The S-equol composition can be an additive component of a food composition (which includes also beverages). The food composition can comprise a probiotic food, a prebiotic food, or a dietary food product. Typically the food product will contain S-equol at a level of from at least 1 mg per serving size to about 100 mg per serving size, but more typically 5-50 mg S-equol per serving size.

The food composition of the invention can also comprise S-equol as a component of a non-racemic mixture of (±)equol as herein described.

Example compositions according to the present invention can comprise one or more pharmaceutically-acceptable or industrial standard fillers. The filler must not be deleterious to a subject treated with the composition. The filler can be solid or a liquid, or both. The filler can be formulated with the active S-equol as a unit-dose, for example a tablet, which can typically contain from about 10% to 80% by weight of S-equol. Compositions can be prepared by any of the well known techniques of pharmacy, for example admixing the components, optionally including excipients, diluents (for example water) and auxiliaries as are well known in the pharmaceutical field.

Compositions suitable for oral administration can be presented in discrete units, such as capsules, cachets, lozenges, or tablets, each containing a predetermined amount of the extract; as a powder or granules; as a solution or a suspension in an aqueous or non-aqueous liquid; or as an oil-in-water or water-in-oil emulsion. Such compositions can be prepared by any suitable method of pharmacy which includes the step of bringing into association the active S-equol and one or more suitable carriers (which can contain one or more accessory ingredients as noted above). In general the compositions of the invention are prepared by uniformly and intimately admixing the S-equol with a liquid or finely divided solid carrier, or both, and then, if necessary, shaping the resulting mixture. For example, a tablet can be prepared by comprising or moulding a powder or granules containing the extract, optionally with one or more accessory ingredients. Compressed tablets can be prepared by compressing in a suitable machine, the extracts in the form of a powder or granules optionally mixed with a binder, lubricant, inert diluents, and/or surface active/dispersing agent(s). Moulded tablets can be made by moulding, in a suitable machine, the powdered compound moistened with an inert liquid binder.

Suitable fillers, such as sugars, for example lactose, saccharose, mannitol or sorbitol, cellulose preparations and/or calcium phosphates, for example tricalcium phosphate or calcium hydrogen phosphate, and also binders such as starch pastes using, for example, corn, wheat, rice or potato starch, gelatin, tragacanth, methylceullose and/or polyvinylpyrrolidone, and, if desired, disintegrators, such as the above-mentioned starches, also carboxymethyl starch, cross linked polyvinyl pyrrolidone, agar or alginic acid or a salt thereof, such as sodium alginate. Excipients can be flow conditioners and lubricants, for example silicic acid, talc, stearic acid or salts thereof, such as magnesium or calcium stearate, and/or polyethylene glycol. Dragee cores are provided with suitable, optionally enteric, coatings, there being used, inter alia, concentrated sugar solutions which can comprise gum arabic, talc, polyvinylpyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropylmethylcellulose phthalate. Dyes or pigments can be added to the tablets or dragee coatings, for example for identification purposes or to indicate different doses of active ingredients.

Other orally administrable pharmaceutical compositions are dry-filled capsules made, for example, of gelatin, and soft, sealed capsules made of gelatin and a plasticiser, such as glycerol or sorbitol. The dry-filled capsules can comprise the extracts in the form of granules, for example in admixture with fillers, such as lactose, binders, such as starches, and/or glicants, such as talc or magnesium stearate, and, where appropriate, stabilizers. In soft capsules, the extract is preferably dissolved or suspended in suitable liquids, such as fatty oils, paraffin oil or liquid polyethylene glycols, to which stabilizers can also be added.

For use in the fortification of food, the S-equol can be mixed with a wide range of food products or food components, including cereal, yogurt, soymilk, soup, cheese, pasta, spread, candy bar, sports bar, drinks, or dairy products.

Formulations suitable for buccal (sublingual) administration include lozenges comprising the extracts in a flavored-base, usually sucrose and acacia or tragacanth; and pastilles comprising the compound in an inert base such as gelatin and glycerin or sucrose and acacia.

Formulations suitable for rectal administration are preferably presented as unit dose suppositories. These can be prepared by admixing the isoflavones with one or more conventional solid carriers, for example cocoa butter, and then shaping the resulting mixture.

Compositions Containing R-Equol

A composition of the present invention can comprise R-equol, and typically consists essentially of R-equol. The composition is used in making commercial and institutional products. The composition, or a product or article of commerce made therefrom, can be consumed orally or applied topically.

The product can comprise any of the products described herein above related to the S-equol, with R-equol at dose levels and composition levels that are the same as those for S-equol.

The R-equol can also be an equol conjugate, conjugated at the C-4' or the C-7 position with a conjugate selected from the group consisting of glucuronide, sulfate, acetate, propionate, glucoside, acetyl-glucoside, malonyl-glucoside, and mixtures thereof.

A composition or preparation comprising R-equol that is administered to subjects for the treating and/or prevention of, or for reducing the predisposition to, diseases and conditions related thereto can also comprises one or more pharmaceutically acceptable adjuvants, carriers and/or excipients, and in the product forms, as described above related to the S-equol.

The composition can typically be made by isolating the R-equol enantiomer from a racemic mixture of R-equol and S-equol, as described above related to the S-equol.

Identifying Equol Producers and Non-Equol Producers

Figure 2:
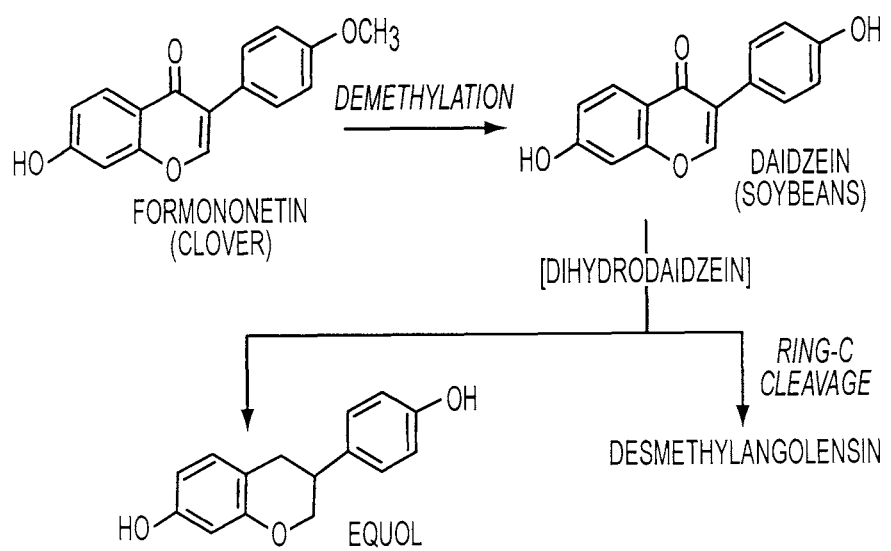
FIG. 2 shows a chemical reaction scheme wherein formononetin and daidzein are converted to equol.

Studies in healthy adults using [$^{13}$C]daidzein and [$^{13}$C]genistein tracers show conclusively that equol is formed from daidzein, and not genistein. Equol is formed following the hydrolysis of the glycoside conjugates of daidzein from soy, and the methoxylated isoflavone formononetin, or its glycosidic conjugates found in clover. In all cases the reaction proceeds through a dihydro-intermediate, as shown in FIG. 2. Once formed, equol appears to be metabolically inert, undergoing no further biotransformation, save phase II metabolism or a minor degree of additional hydroxylation in the liver. As with daidzein and genistein, the predominant phase II reactions are glucuronidation and, to a minor extent, sulfation. Following the original discovery that equol's presence in urine was a function of soy food ingestion, it was observed that approximately 50-70% of the adult population did not excrete equol in urine even when challenged daily with soy foods, for reasons that are unclear. Furthermore, even when the pure isoflavone compounds are administered, thereby removing any influence of the food matrix, it has been shown that many people do not convert daidzein to equol. This phenomenon has led to the terminology of a person being an 'equol-producer' or 'non-equol producer' (or 'poor equol-producer') to describe these two distinct populations.

Cut-off values have been empirically derived permitting assignment of individuals to each of these categories. People who have plasma equol concentrations of less than 10 ng/mL (40 nmol/L) can be classified as 'non-equol producers' and where levels are above 10 ng/mL (40 nmol/L) this defines 'equol producers'. This distinction can also be derived from the levels in urine, an equol producer being someone excreting greater than 1000 nmol/L. Although the excretion of equol is highly variable among individuals there is a large demarcation between those that can produce equol and those that cannot, consistent with a precursor-product relationship in enzyme kinetics catalyzing the reaction. There is consequently an inverse relationship between urinary daidzein and equol levels, and thus far no significant gender differences have been defined.

The status of a subject as an equol producer or a non-equol producer is important in the recruitment of subjects for clinical research evaluating the administering of isoflavones, and particularly daidzein, genistein, formononetin and biochanin A. For example, a number of bone and soy feeding studies have been performed with variable outcomes. Short-term studies, of 12 weeks or less, where surrogate markers of bone-turnover such as urinary pyridinoline and deoxypyrodinoline cross-links, plasma/serum osteocalcin, alkaline phosphatase, and IGF-1 have indicated reduced bone turnover when soy foods containing isoflavones were included in the diet. Several clinical studies of nine-month duration or less have been reported to show a bone-sparing effect. All measured changes in bone mineral density (BMD) at various sites and the results were conflicting, with 2 of the four showing no effect. In all but one study, there has not been an attempt to define equol status. In that one study, being an equol-producer was found to be associated with a significantly increased BMD when soy foods were consumed over a 2-year period. Thus, based on our data, equol is a bone-trophic agent and therefore identifying a subject as an 'equol-producer' has therapeutic implications, while delivering equol will be beneficial in preventing bone loss and increasing bone formation.

The invention includes a method of conducting research wherein an isoflavone is administered to a human subject and at least one physiological datum is measured, comprising the steps of: 1) administering to at least one human subject of a selected group of subjects, a dose of an isoflavone that is a precursor to equol, 2) detecting the level of equol in the urine or blood of the subject, and 3) identifying the subject as either an equol producer or a non-equol producer. The physiological datum is typically one that can be affected by the estrogenic activity of the isoflavone. Having identified a subject as either an equol producer or a non-equol producer, data collected from the research study can be analyzed distinctly, whereby the data of one or more subjects identified as equol producers can be collected, separated, analyzed or reported separately from the data of one or more subjects identified as non-equol producers. Subjects identified as either an equol producer or a non-equol producer can be excluded from (or included in) the group of research subjects.

Chemical Synthesis of Equol:

In this process standard chemical treatments are used to hydrogenate the double-bond of the heterocyclic ring and to remove the carbonyl at position C-3. Typical starting materials are isoflavones such as daidzein, genistein, glycitein, peurarin, formononetin and biochanin A and their glucoside conjugates. Any conjugated form would be reduced to its aglycon by hydrolysis as defined above. Suitable solvents for the reaction include organic acids such as glacial acetic acid, lower alcohols such as isopropanol, and mixtures thereof. Reduction catalysts typically employed include Palladium, such as 10% Pd on charcoal. Reactions can run at temperatures from ambient to 60° C., with pressures ranging from slightly above ambient, up to 200 psig (14 atm. gauge), and with reaction times of up to 30 hours or more.

After reaction completion, the catalyst is removed and any filtrate evaporated. The crude residue is purified, typically by chromatography employing a silica gel column, with an eluent comprising C2-C4 alcohols, C3-C7 alkanes, and mixtures thereof. The purified residue can be crystallized from n-hexane to produce (±)equol as a pure product, typically of at least 99%, with a yield typically of at least 75%. The equol crystallized product is colorless, not hygroscopic, and stable in air, and does not decompose during the final filtration procedure.

The equol product can be authenticated by GC-MS analysis of the trimethylsilyl ether, or tert-butyldimethylsilyl ether, or any other volatile derivative of synthesized product as a single pure peak and a mass spectrum that is consistent with the published electron ionization spectrum of the trimethylsilyl (TMS) ether derivative of authentic equol.

Method for the Isolation of the Individual R- and S-Enantiomers from Racemic Equol The invention also relates to a method of separating a racemic mixture of equol into its two distinct enantiomers. The method uses a mixture of racemic equol, typically obtained from a chemical synthesis, as provided above. A quantity of the racemic equol is introduced into an inlet of the HPLC column with a mobile phase comprising a C4-C8 alkyl and a C2-C4 alcohol. After a first period of time from passing the racemic mixture into the inlet the time period depending upon the type of column, type of eluent, eluent flow rate, temperature, and mass of the racemic mixture, a first effluent is collected from an outlet of the HPLC column. The first eluent will comprise the first enantiomer, typically S-equol. After a second period of time from passing the racemic mixture into the inlet, the time period depending upon the type of column, type of eluent, flow-rate, temperature, and mass of the racemic mixture, a second effluent is collected from an outlet of the HPLC column. The second eluent will comprise the second enantiomer, typically R-equol.

The separation of equol into S-equol and R-equol can be done on a chiral-phase column. A typical example of a chiral-phase column is a Chiralcel OD column or OJ column, supplied by Daicel Chemical Industries Ltd. Columns for separation of marketed quantities of enantiomers can be produced on industrial systems comprising product and mobile phase pumps, industrial-sized columns, utilities, and control systems. The mobile phase comprises C3-C7 alkanes or a similar polarity solvent, C2-C4 alcohols, and mixtures thereof. The mobile phase typically comprises a 95:5 to 5:95, more typically a 50:50 to 90:10, ratio of hexane to a propanol. A typical example of a mobile phase comprises 70% hexane and 30% ethanol.

The elution of an equol enantiomer from the column can be detected by UV absorbance at 260-280 nm or by a more specific detection system such as a mass spectrometer and monitoring of ions specific to equol. The conditions will be optimized to afford complete separation of S-equol and R-equol enantiomers as demonstrated by analytical HPLC.

The chiral-phase column typically comprises a silica substrate to which is attached a material for selectively separating enantiomers of equol. A typical selection material comprises a cellulose tris(3,5-dimethylphenyl carbamate) and a cellulose tris(4-methylbenzoate).

Biological Production of S-Equol

S-equol can be produced in bulk, and can be produced in situ in a variety of food products, using conventional food technology. A base solution media, food product or plant extract can be provided that comprises daidzein or another related isoflavone from which daidzein can be derived. The daidzein or other isoflavone can be converted to S-equol by a standard bacterial or enzyme fermentation process, to provide a bulk solution, food product or plant extract that comprises S-equol.

The production of S-equol in a food product can be achieved by utilizing the metabolic activity of bacteria growing on the food that contains a satisfactory starting material, such as daidzin, daidzein, formononetin or peurarin, or a conjugate or mixture thereof. As shown in FIG. 2, the conversion of daidzein to equol involves three major steps: 1) hydrolysis of any glucoside conjugate group, 2) conversion of the isoflavone aglycons to a dihydro-intermediate, and 3) conversion of the dihydro-intermediate to equol. The metabolic pathway and enzymes for each of the three steps required may not necessarily be present in one bacterium. Anecdotal evidence from human studies suggests that there may be one or more bacteria that act in conjunction to perform these reactions, as evidenced from the fact that often dihydrodaidzein can be present in significant amounts in plasma and urine yet equol may be low or barely detectable. Although equol may be produced from daidzein by a single organism it is believed that better or more efficient conversion can be achieved when using a mixture of bacterial species, each with its own metabolic profile. Important conditions for effective conversion to S-equol include the selection of the bacterial organism or mixture of organisms, the temperature of incubation, and the amount of oxygen available to the organisms. These conditions can be optimized by techniques well known to persons skilled in this art. The organisms used to effect this change can be inactivated by standard techniques used in the food industry or, alternately, allowed to remain in an active state in the product.

Bacteria useful in a fermentation process to convert daidzein and/or other structurally related isoflavones, or an intermediate compound, to S-equol, can include a bacterial strain or bacterial strains found to colonize the intestinal tract of a human, horse, rodent, or other mammal that is an 'equol producer'. Since intestinal bacteria in mammals are found in feces, the equol-producing bacteria can also be found in the feces of 'equol producing' mammals.

Typical bacteria useful in a fermentation process should demonstrate an optimized conversion rate and extent of conversion that makes the biological production of equol efficient.

Typically, one or more bacterial strains are required to convert the daidzein (or other related isoflavone) through intermediate products to S-equol, which generally involves one or more of the three major reactions: the conversion of isoflavone glycone to aglycon isoflavone; the conversion of aglycon isoflavone to dihydro isoflavone; and the conversion of dihydro isoflavone to the product, equol. For example, a mixed culture of organisms isolated from equine feces and a mixed culture of organisms derived from the gastrointestinal tract of a person known to an 'equol producer' can convert, as they do in vivo, the glycone daidzein to the final product S-equol.

Typical bacterial strains that can convert a glycone to an aglycon (such as daidzein to daidzein) include *Enterococcus faecalis*, a *Lactobacillus plantarum*, *Listeria welshimeri*, a mixed culture of organisms isolated from the intestinal tract of an 'equol producing' mammal, *Bacteriodesfragilis*, *Bifidobacterium lactis*, *Eubactria limosum*, *Lactobacillus casei*, *Lactobacillus acidophilous*, *Lactobacillus delbrueckii*, *Lactobacillus paracasei*, *Listeria monocytogenes*, *Micrococcus luteus*, *Proprionobacterium freudenreichii* and *Sacharomyces boulardii*, and mixtures thereof.

Typical bacterial strains that can convert an aglycon to equol (such as daidzein to S-equol) include *Proprionobacteria freundenreichii*, a mixed culture containing: *Bifidobacterium lactis*, *Lactobacillus acidophilus*, *Lactococcus lactis*, *Enterococcus faecium*, *Lactobacillus casei* and *Lactobacillus salivarius*; and a mixed culture of organisms isolated from the intestinal tract of an 'equol producing' mammal.

The time required for bacterial conversion of the glucosides to aglycons, or the aglycons to the equol product, will depend upon bacteria-related factors, particularly concentration, the availability of oxygen, and the temperature and pH of the incubating system. In most instances it is possible to achieve substantially complete conversion within 24 hours.

The pH range for bacterial conversion of the isoflavone glucosides to aglycon isoflavones is from about 3 to about 9. The optimum pH depends primarily upon the type of bacteria used, and should be selected accordingly.

The time required for enzymatic conversion of the glucosides to aglycons, and aglycons to the equol product, depends upon enzyme-related factors, particularly concentration, and the temperature and pH of the system. In most instances it is possible to achieve substantially complete conversion within 24 hours, more preferably within about 2 hours, and most preferably within about 1 hour.

In an alternative approach to producing equol biologically, S-equol can be produced in situ in a food product or other suitable substrate by an enzymatic conversion of daidzein or other structurally related isoflavone to S-equol. Suitable enzymes can be separated and concentrated from bacteria that are effective at converting daidzein or structurally related isoflavones to equol, using standard techniques for separating and purifying such enzymes. These are well know and used by practitioners of the art and science of enzymology and biochemistry. The equol production can be achieved with efficient conversion without requiring growth of bacteria in the food itself.

Enzymes useful in a process to convert daidzein and/or other related isoflavones, or an intermediate compound, to equol, can include an enzyme isolated from a bacteria, or a mixture of bacteria, that have been shown to convert a suitable isoflavone to equol. An examples of such bacteria or mixtures of bacteria can include, but is not limited to, bacteria found to colonize the intestinal tract of a human, horse or other mammal that is an 'equol producer'. Typical enzymes useful in a process to convert daidzein or an intermediate compound to equol should demonstrate an optimized conversion rate and extent of conversion that makes the biological production of equol efficient.

Enzymes that can be used can be isolated from one or more, or from a mixture of, the bacteria described herein for converting daidzein or a structurally related isoflavone, or an intermediate compound, to equol.

In a typical method, bacteria are cultured in a nutritive tryptone broth anaerobically at about 37° C. for about 15 hours to about 72 hours, more typically from about 24 hours to 36 hours. The bacteria are then separated from the culture broth by conventional techniques, most commonly by centrifugation at a gravitational force from about 1500 g, up to and in excess of 25,000 g. The cells are washed in saline solution (from about 0.1%, up to about 5%, and preferably at about 0.9%) by suspending them in the saline, and re-centrifuging the suspension. The washed, separated cells are used to prepare an extract of active enzymes using techniques well know to those practiced in the art of enzymology and biochemistry. The crude enzyme mixture can be used as-is as an enzyme extract, or can be further purified by conventional enzyme preparation techniques.

A prepared enzyme extract is added to a food containing a suitable isoflavone, such as daidzein, daidzin, or formononetin. Other isolated enzymes, some of which are commercially available, can be added to speed up the conversion of starting material to intermediates in the enzyme mediated reaction pathway. The product is typically incubated at a temperature from about 25° C. to about 45° C., preferably from about 30° C. to about 40° C., while maintaining mild anaerobic conditions in the samples being grown. The rate of conversion of the daidzein type compounds to equol is dependent on the amount of active enzyme added to the food base. Best results are obtained when conversion proceeds rapidly (substantially complete in about 2 hours), but longer times for conversion are necessary at low enzyme activities. The amount of equol produced in the food may be controlled either by limiting the amount of daidzein containing compounds in the food or by inactivating the enzymes at an appropriate time after incubation commences, for example by heating the resulting food product to about 95° to 100° C.

The first step in the enzymatic preparation of S-equol is the conversion of the glucoside to the aglycon. As an alternative to using enzymes isolated in the manner described above to effect this conversion, it is possible to use commercially available enzymes. The enzymatic conversion of glucosides to aglycons can be performed by bringing a suitable enzyme into contact with the isoflavone glucosides at a suitable pH and temperature. The conversion of isoflavone glucosides to aglycon isoflavones has been found to be dependent on a variety of factors including the type of enzymes used, activities of the enzymes, and the pH and temperature of the incubated solution during the conversion. The enzymes required to effect the conversion are enzymes capable of cleaving the glucosidic linkage between the isoflavone moiety and the glucose molecule of the isoflavone glucosides. In a preferred embodiment, the enzymes are saccharidase or gluco-amylase enzymes capable of cleaving 1,4-glucoside bonds.

Such enzymes are commercially available alpha- and beta-glucosidase enzymes, beta-galactosidase enzymes, gluco-amylase enzymes, and pectinase enzymes. Typical examples of these enzymes include Biopectinase 200AL (which is preferably utilized at a pH range of from about 2.5 to about 6.5), available from Deltagen, Redwood City Calif., Biolactase 30,000 (optimum pH range from about 3 to about 6) Neutral Lactase (optimum pH range from about 6 to about 8), both of which are available from Quest International, 1833 57th Street, Post Office Box 3917, Sarasota, Fla. 34243. Other particularly preferred supplemental enzymes include Lactase NL (optimum pH from about 6 to about 8) and Enzeco Fungal Lactase Concentrate (optimum pH from about 4.5 to about 6.5) available from Enzyme Development Corporation, 2 Penn Plaza, Suite 1102, 360 West 31$^{st}$ Street, New York, N.Y. 10001; β-galactocidase from *E. coli* (optimum pH from 6.0 to 8.0), manufactured by Worthington Biochemicals and available from ScimaR, 4 Ruskin Close, Templestowe, Victoria. 3106, Australia; Lactozyme 3000L (which preferably is utilized at a pH range from about 6 to about 8), and Alpha-Gal 600L (which preferably is utilized at a pH range of from about 4 to about 6.5), available from Novo Nordisk Bioindustrials, Inc., 33 Turner Road, Danbury, Conn. 06813; Maxilact L2000 (which is preferably utilized at a pH range of from about 4 to about 6), available from DSM Food Specialties PO Box 1, 2600MA, Delft, The Netherlands.

The pH range for conversion of the isoflavone glucosides to aglycon isoflavones is from about 3 to about 9. The pH that is utilized depends primarily upon the type of enzyme used, and should be selected accordingly. The enzymes are active within an optimum pH range specified by the manufacturer of the enzyme, as shown above for several specific enzymes. Typically the enzymes are active either in a neutral pH range from about 6 to about 8, or in an acidic pH range from about 3 to about 6.

The temperature range of an isoflavone-rich material for the conversion of glucosides to aglycons is from about 5° C. to about 75° C. The temperature significantly affects the activity of the enzymes, and therefore, the rate of conversion. The enzymes may be active above 70° C., for example Alpha-Gal 600L is active at 75° C. However, it is preferred to conduct the conversion at lower temperatures to avoid enzyme deactivation. In a preferred embodiment, the conversion is conducted at a temperature between about 35° C. to about 45° C.

The time required for conversion of the glucosides to aglycons depends upon enzyme-related factors, particularly concentration, and the temperature and pH of the system. In most instances it is possible to achieve substantially complete conversion within 24 hours, however, it is preferred that the enzyme be added to dramatically increase the rate of the reaction. The selected enzyme, enzyme concentration, pH and temperature preferably cause substantially complete conversion within about 2 hours, and most preferably within about 1 hour.

Use of *Helix Pomatia* as a β-Glucosidase

The invention also relates to a novel method of enyzmatically hydrolyzing a glucoside, and in particular an isoflavone glucoside, comprising contacting the glucoside with an enzyme-containing extract from *Helix pomatia* for a time, and under conditions, sufficient to convert the glucoside to the corresponding aglycon. The enzyme-containing extract is typically the digestive juice of *Helix Pomatia*.

In the course of synthesizing equol from its isoflavone glucoside starting material, it was discovered that the digestive juice of *Helix pomatia* effectively serves as a β-glucosidase for converting an isoflavone glucoside to the aglycon isoflavone. *Helix pomatia* digestive juice is commercially marketed as a β-glucuronidase and sulfatase preparation and has for thirty years been the enzyme preparation of choice for hydrolysis of steroid and isoflavone conjugates. Its use as a β-glucosidase was unknown and unexpected. The β-glucosidase activity is sufficiently capable of completely hydrolyzing in vitro isoflavone conjugated with sugar moieties.

The digestive juice can be used as-is, or in a purified form. The efficiency of *Helix pomatia* digestive juice to hydrolyze isoflavone glycosides was established by incubating in vitro 100 μg each of daidzin and genistin with 0.1 mL of *Helix pomatia* digestive juice suspended in 10 mL of 0.05M sodium acetate buffer, pH 4.5 at 37° C. Before adding the enzyme/buffer mixture, it was passed through a solid-phase $C_{18}$ Bond Elut cartridge to remove residual amounts of isoflavones that we have previously found to naturally occur in this enzyme preparation. The concentrations of daidzin and genistin remaining, and daidzein and genistein formed during incubation were determined by HPLC on aliquots of the mixture removed at timed intervals over the next 24 hours.

Figure 3:
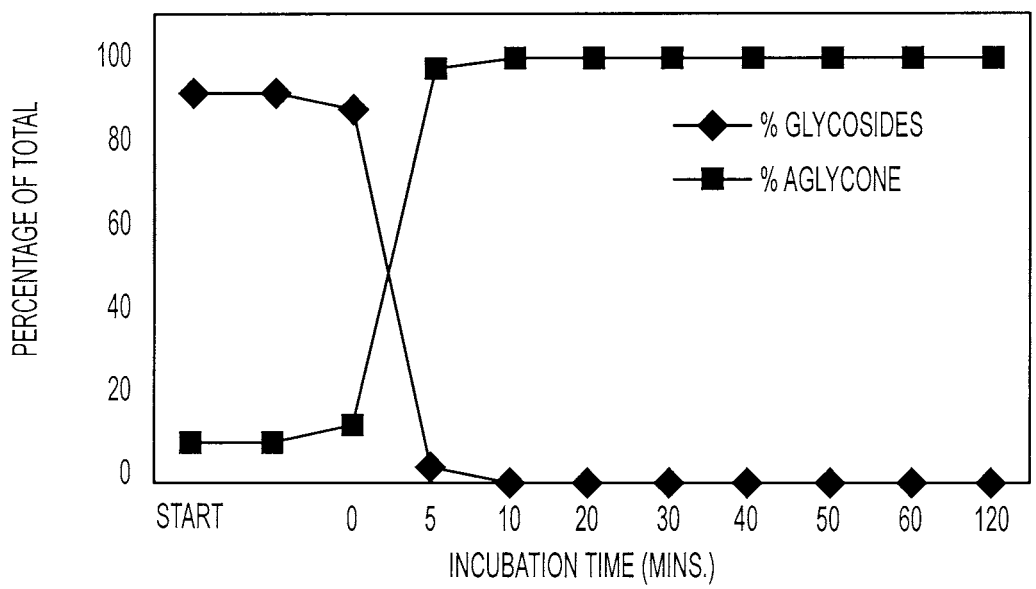
FIG. 3 shows the rate of hydrolysis of isoflavone glycosides from soy germ by incubation with enzymes present in *Helix pomatia* digestive juice.

FIG. 3 shows the time course for the hydrolysis of daidzin and genistin by *Helix pomatia* as measured by HPLC from the proportion of glycosides to aglycons remaining in the incubation mixture. These in vitro studies show that under the analytical conditions employed *Helix pomatia* completely hydrolyzed daidzin and genistin within 15 min and this enzyme preparation in addition to having β-glucuronidase and sulfatase activity is also a useful source of β-glucosidases.

Separation of S-Equol from Bulk Solution

S-equol produced in bulk can be separated from the resulting bulk solution of a bacterial or enzymatic production of S-equol, by methods well known in the art, including crystallization, solvent extraction, distillation, and precipitation/filtration. The resulting bulk solution can contain unreacted daidzein or other related isoflavone used, by-products, and any reactants. Such methods can include the use of a reverse-phase or straight-phase liquid chromatography column and these can be combined with chiral-phase chromatography A typical method of removing S-equol from a bulk solution or solid phase is by extraction. An extractant solution is added to the solution or solid phase containing the S-equol. Typically the extractant is a low molecular weight alcohol such as methanol, ethanol, isopropyl alcohol, or propyl alcohol, or an aqueous solution having a pH in the range from 3.5 to 5.5. Typically, if the aqueous alcohol method is being used, sufficient alcohol is added to bring the alcohol/water ratio to between a minimum of 40:60 and a maximum of 95:5. More typically, the ratio is at least 60:40, and even more typically a ratio between 65:35 and 90:10.

If an aqueous acid extraction method is used an aqueous acid solution is prepared with the pH adjusted to about 3.5 to about 5.5, and more preferably within the pH range of about 4.0 to about 5.0. Sufficient water is added to make a dilute liquid with a sufficiently low viscosity to permit separation of solids from liquids by centrifugation or filtration.

The liquid, from which insoluble solid matter has been removed, is concentrated by conventional methods for removing liquids. Methods used typically include, but are not limited to, removal of solvent by evaporation, preferably under reduced pressure. The residual liquid is concentrated to at least about 15% solids, and up to about 55% solids, more typically to between 30% and 50% solids. The concentrate is then diluted with water to reduce the solids content and increase the water to alcohol ratio. The amount of water added can be varied over a wide range, though a final solids content between 6% and 15%, and more typically about 13%, is preferred. The pH of the mixture is adjusted between about pH 3.0 and about pH 6.5, with a preferred value between about pH 4.0 and about pH 5.0. Typically the temperature is between about 2° C. to about 10° C., and more typically about 5° C. to 7° C.

The solid material is then separated from the liquid by standard separation techniques (centrifugation or filtration) and yields an equol-rich solid material.

The equol-rich material can optionally be purified, typically by chromatography employing a silica gel column, with an eluent comprising C2-C4 alcohols, C3-C7 alkanes, and mixtures thereof. The purified residue can be crystallized from n-hexane to produce S-equol as a pure product, typically of at least 99%, with a yield typically of at least 75%. The equol crystallized product is colorless, not hygroscopic, and stable in air, and does not decompose during the final filtration procedure.

The S-equol product can be authenticated by GC-MS analysis of the trimethylsilyl ether or tert-butyldimethylsilyl ether derivative, or some other appropriate volatile derivative of synthesized product as a single pure peak and a mass spectrum that is consistent with the published electron ionization spectrum of the trimethylsilyl (TMS) ether derivative of authentic equol. Confirmation of the product can also be established by direct mass spectrometry using electrospray ionization after introducing the sample into the instrument via an HPLC chiral-phase column.

Treatment of Disease by Administering S-Equol

This present invention provides a means for an individual subject to overcome the problem of not being able to produce equol in vivo, by providing delivery of equol enantiomers, and specifically S-equol or mixtures of S-equol and R-equol directly, circumventing the need for intestinal bacteria for its production. The delivery of S-equol can also supplement the in vivo production of S-equol in 'equol-producers', as well as in 'non-equol producers'.

This invention provides a method for delivering S-equol in sufficient amounts to have health benefits. The active S-equol material can be delivered by direct ingestion or administration of the pure S-equol compound or any conjugated analog of S-equol. Typically, the amount of composition comprising S-equol is administered in an amount sufficient to produce a transient level of S-equol in the blood plasma of the mammal of at least 5 nanograms per milliliter (ng/mL), more typically at least 10 ng/mL or greater, or transient levels of S-equol in urine of greater than 1000 nmol/L. The S-equol can also be an S-equol conjugate, conjugated at the C-4' or the C-7 position with a conjugate selected from the group consisting of glucuronide, sulfate, acetate, propionate, glucoside, acetyl-glucoside, malonyl-glucoside, and mixtures thereof. Typically, the composition is administered orally in a dose amount of at least about 1 mg, more typically of at least 5 mg, and of up to 100 mg, more typically, up to 50 mg.

The ability to deliver the S-equol in sufficient amounts is believed to provide several advantages over delivery of a racemic mixture of equol. First, the potency of S-equol is expected to be at least twice that of the racemic mixture. Second, the human body only produces the S-equol, and therefore, a composition comprising only S-equol represents a "natural" product with an ingredient, S-equol, with which the body is familiar. And third, since it is believed that the R-equol enantiomer is not produced by the human body, a treatment composition comprising only, or substantially only, the S-enantiomer does not introduce a material with which the body is unfamiliar.

Compositions of the present invention can be used to treat a variety of hormone-dependent diseases and conditions associated therewith.

The invention includes the use of S-equol to treat and prevent diseases and conditions including brain disorders, dementia of the Alzheimer type, as well as other reduced or impaired cognitive functions associated with advancing age and with short- and long-term memory loss. The estrogenic activity of S-equol acts in the brain by enhancing neurotransmission and restoring synaptic density. It is believed that S-equol is active in the brain at the same site as estrogen, exerting an estrogenic response.

The invention includes the use of S-equol to treat and prevent osteopenia and osteoporosis.

In a two-year randomized study, postmenopausal women consumed each day two glasses of soymilk, either with or without isoflavones. The data found that lumbar spine BMD and BMC decreased 4.0% and 4.3%, respectively (p<0.01) over the 2 year period in the group consuming soymilk with negligible amounts of isoflavones. These levels are close to the 5-7% loss in bone mass that would be normally expected in the first two years of natural menopause. By contrast, those women consuming soymilk that contained 50 mg isoflavones showed an increase of 1.1% and 2% in lumbar spine BMD and BMC respectively (relative to baseline values). This study showed that soy protein with isoflavones, as opposed to lacking in isoflavones, maintained stable bone mass over a 2-year period. The data suggests that bone loss as measured by changes in lumbar spine BMD was prevented by the presence of isoflavones.

It should be mentioned that this difference was not observed after only one year. Given the slow rate of bone turnover the variability in data from previous bone studies is likely to be a consequence of the short duration of dietary intervention with soy foods.

The most striking observation was that women who were 'equol-producers', defined by a plasma equol concentration of greater than 10 ng/mL (45% of the cohort), showed mean increases of 2.4% and 2.8% respectively for bone mineral density (BMD, p=0.02) and bone mineral content (BMC, p=0.009) in the lumbar spine, compared with increases of only 0.6% and 0.3%, respectively in women in the 'non-equol producing' group. Women administered a control substance showed mean decreases of 4.0 and 4.3%, respectively (p<0.01 compared to baseline). This data demonstrates that the ability to metabolize isoflavones to produce equol, and the presence of equol in the body, have a direct relation to increased BMD and BMC. These data suggest that equol is an important bone-trophic agent. The composition comprising S-equol is administered in an amount sufficient to reduce the surrogate markers of bone turnover, or prevent bone loss as measured by bone mineral density. The composition comprising S-equol can also be administered in an amount sufficient to increase bone formation, or to prevent osteoporosis and reduce bone fracture.

The invention includes the use of S-equol to treat and prevent lipid disorders such as high cholesterol (hypercholesterolemia), lipidemia, lipemia and dyslipidemia (disturbances in lipids). The study described above also included the study of the cholesterol concentrations in the test subjects. The results showed that plasma total cholesterol concentrations decreased 7.2% (p=0.04) in equol producers compared with baseline levels and 3.0% (p=NS) in non-equol producers. The failure of soy protein to have significant cholesterol-lowering effects in adults with normal blood cholesterol levels, is, with few exceptions, probably because of heterogeneity in the study populations with regard to the metabolism of soy isoflavones and the failure to recognize the relevance of equol formation. These data suggest that equol influences lipids in a favorable manner. The composition comprising S-equol is administered in an amount sufficient to reduce the level of lipids in the blood stream.

The invention also includes the use of S-equol to treat and prevent acute and chronic ovarian estrogen deficiency states including, vasomotor disturbances and night sweats, commonly referred to as 'hot flushes' or 'hot flashes'. This also includes hot flushes accompanying antiestrogen therapy used in the treatment of breast cancer.

The invention also includes the use of S-equol to treat and prevent cardiovascular disease and liver disease.

The invention further includes the use of S-equol to improve diminished blood vessel quality, by increasing reactivity or flexibility in response to acute changes in blood pressure, improving blood flow, and reducing blood pressure.

The invention includes the use of S-equol to reduce lipid peroxidation and act as an antioxidant in scavenging free-radicals in the body.

The invention also includes the use of S-equol to reduce inflammation as evidenced by effects on reducing markers of inflammation such as C-reactive protein.

The invention also includes the use of S-equol to treat and prevent cancer, including benign breast cancer, breast cancer, benign prostate cancer, prostate cancer, skin cancer, and colon cancer. The invention also includes methods of delivering S-equol to a manner to prevent or treat benign prostatic hyperplasia or an associated condition.

The invention also includes the use of S-equol to treat and prevent adenomatous polyps and familial polyposis, both of which are high-risk conditions predisposing to colon cancer. Given the important role of estrogen in reducing colon cancer risk in women, it is reasonable to expect enantiomers of equol to have similar preventive or therapeutic actions, especially as the colon is the major site of equal production from its precursors.

Compositions of the present invention can be used to treat a variety of non-hormone-dependent diseases and conditions associated therewith, including inflammatory conditions of the gastrointestinal tract, the prostate, the breast, the skin and bone.

The presence of a chiral center in the equol molecule may have relevance to its biological potency. The efficacy of the enantiomers will be greater than the racemate, especially toward ERβ.

In the method of this invention, calcium, or vitamin D can be co-administered (that is before, at the same time or after the S-equol), for example as a separate tablet, or as part of a suitable dosage form.

Equol possesses other properties of relevance to cellular function. Being a polyphenol it shares with flavonoids the ability to be a hydrogen/electron donor and therefore may scavenge free radicals. Equol has the greatest antioxidant activity of all the isoflavones tested when measured in vitro in the FRAP, TEAC and Cu(II)-induced or ferric(III)-induced liposomal peroxidation assays. Although isoflavones are considered weak antioxidants when tested in vitro, their in vivo effect may be significant enough to account for the reduced ex vivo lipid peroxidation that has been observed in all but one clinical study when adults consume soy protein diets. Given the superior antioxidant activity of equol over other isoflavones, a case can be made for being an 'equol-producer' or in those people unable to make equol for delivering directly equol either as a pharmacologic agent, a supplement or in a food product. In all cases enhanced circulating equol levels can provide greater inhibition of lipid peroxidation and therefore greater reduction in risk for cardiovascular disease.

It is believed that non-equol producers are generally at a higher risk than equol producers for developing certain diseases, typically hormone-dependent diseases or conditions, including breast cancer. For those humans who are poor- or non-equol-producers, comparable benefits may be attained by oral, topical, nasal, subcutaneous, or intravenous administration of equol enantiomers or mixtures thereof.

Supplementing the diet of the equol producers with equol, and particularly the S-equol, can provide benefits when the ordinary level of S-equol produced by the equol producer is inadequate because of 1) insufficient consumption of isoflavones to produce equol, 2) antibiotic use that wipes out the activity of intestinal bacteria to make equol from precursor isoflavones, or 3) other health factors that impact the level of equol production. In addition, a supplemental level of equol, and particularly S-equol, is believed to provide enhanced effect on the health and well-being of the person.

Treatment of Disease by Administering R-Equol

This present invention also provides a means for an individual subject to overcome the problem of not being able to produce equol in vivo, by providing delivery of equol enantiomers, and specifically R-equol or mixtures of R-equol and S-equol directly, circumventing the need for intestinal bacteria for its production.

This invention provides a method for delivering R-equol in sufficient amounts to have health benefits. The R-equol material can be delivered by direct ingestion or administration of the pure R-equol compound or any conjugated analog of R-equol. Typically, the amount of composition comprising R-equol is administered in an amount sufficient to produce a transient level of R-equol in the blood plasma of the mammal of at least 5 nanograms per milliliter (ng/mL), more typically at least 10 ng/mL or greater, or a transient level of R-equol in urine of greater than 1000 nmol/L. The R-equol can also be an equol conjugate, conjugated at the C-4' or the C-7 position with a conjugate selected from the group consisting of glucuronide, sulfate, acetate, propionate, glucoside, acetyl-glucoside, malonyl-glucoside, and mixtures thereof. Typically, the composition is administered orally in a dose amount of at least about 1 mg, more typically of at least 5 mg, and of up to 100 mg, more typically up to 50 mg.

The ability to deliver R-equol in sufficient amounts is believed in some circumstances, such as breast cancer prevention, or for antagonizing ligand binding to specific ER such as ERβ1 or ERβ2, to provide some advantage over delivery of a racemic mixture of equol.

Compositions of the present invention comprising R-equol can be used to treat a variety of hormone-dependent diseases and conditions associated therewith.

The invention includes the use of R-equol to treat and prevent diseases and conditions including brain disorders, dementia of the Alzheimer type, as well as other reduced or impaired cognitive functions associated with advancing age and with short- and long-term memory loss. It is believed that R-equol is active in the brain at the same site as estrogen, exerting an estrogenic response mediated through specific estrogen receptors that are rich in certain regions of the brain, while also having antioxidant effects in protecting neurons against oxidative stress.

The invention includes the use of R-equol to treat and prevent osteopenia and osteoporosis since antioxidants have protective effects against osteoclast activity.

The composition comprising R-equol is administered in an amount sufficient to reduce the surrogate markers of bone turnover, or prevent bone loss as measured by bone mineral density. The composition comprising R-equol can also be administered in an amount sufficient to increase bone formation, or to prevent osteoporosis and reduce bone fracture.

The invention includes the use of R-equol to treat and prevent lipid disorders such as high cholesterol (hypercholesterolemia), lipidemia and lipemia or dyslipidemia (disturbances in lipids). The failure of soy protein to have significant cholesterol-lowering effects in adults with normal blood cholesterol levels is, with few exceptions, probably because of heterogeneity in the study populations with regard to the metabolism of soy isoflavones and the failure to recognize the relevance of equol formation. These data suggest that equol influences lipids in a favorable manner. The composition comprising R-equol is administered in an amount sufficient to reduce the level of lipids in the blood stream and to reduce lipid peroxidation.

The invention also includes the use of R-equol to treat and prevent acute and chronic ovarian estrogen deficiency states including, vasomotor disturbances and night sweats, commonly referred to as 'hot flushes' or 'hot flashes'. This also includes hot flushes accompanying antiestrogen therapy used in the treatment of breast cancer.

The invention also includes the use of R-equol to treat and prevent cardiovascular disease and liver disease.

The invention further includes the use of R-equol to improve diminished blood vessel quality, by increasing reactivity or flexibility in response to acute changes in blood pressure, improving blood flow, and reducing blood pressure.

The invention includes the use of R-equol to act as an antioxidant in scavenging free-radicals in the body.

The invention includes the use of R-equol to reduce inflammation as evidenced by effects on reducing markers of inflammation such as C-reactive protein and cytokines The invention also includes the use of R-equol to treat and prevent cancer, including benign breast cancer, breast cancer, benign prostate cancer, prostate cancer, skin cancer, and colon cancer. The invention also includes methods of delivering R-equol to a mammal to prevent or treat benign prostatic hyperplasia or an associated condition.

The invention also includes the use of R-equol to treat and prevent adenomatous polyps and familial polyposis, both of which are high-risk conditions predisposing to colon cancer. Given the important role of estrogen in reducing colon cancer risk in women, it is reasonable to expect enantiomers of equol to have similar preventive or therapeutic actions, especially as the colon is the major site of equol production from its precursors.

Experiments (a) Determination of Equol Enantiomer in 'Equol-Producing' Adults

Figure 4:
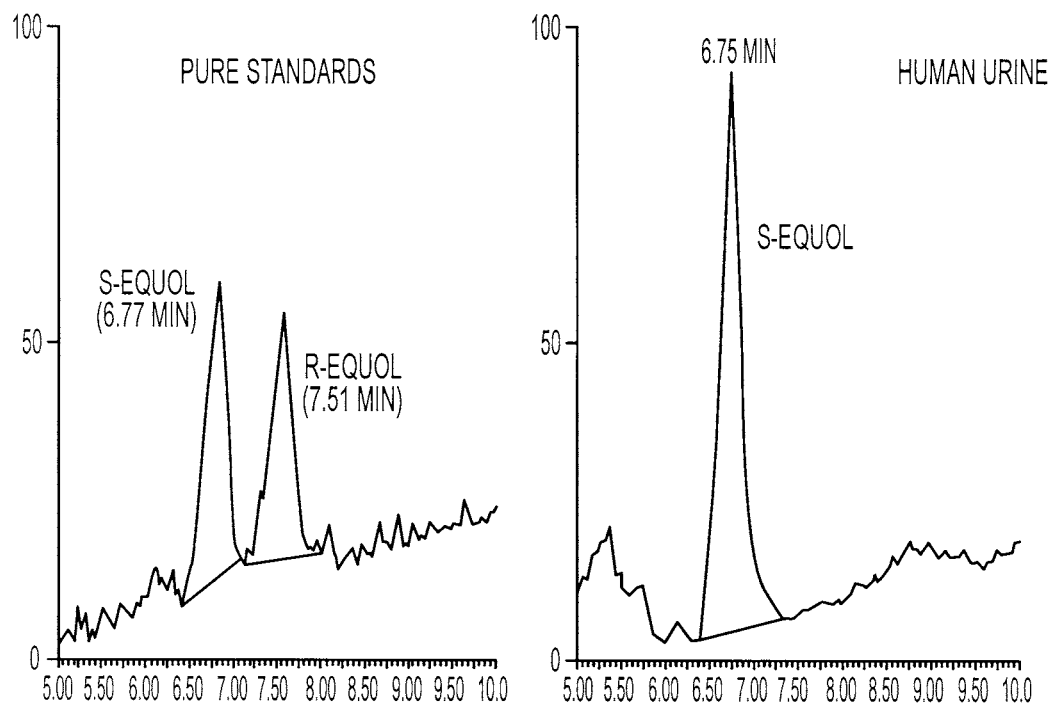
FIG. 4 shows a mass chromatogram of the elution of the equol enantiomers from a sample of urine from an adult consuming soy food, compared against pure enantiomeric standards that had been characterized by optical dichroism.

The urine samples from adults consuming soy foods previously identified as being 'equol-producers' were analyzed. Equol was isolated from urine (25 mL) by passage of the sample through a solid-phase Bond Elut C18 cartridge. After washing the cartridge with water, the isoflavones were recovered by elution with methanol (5 mL) and the methanolic phase was taken to dryness under a stream of nitrogen. The sample was subjected to enzymatic hydrolysis with *Helix pomatia* and then re-extracted on a Bond Elut C18 cartridge. The methanolic extract was taken to dryness under nitrogen gas and redissolved in HPLC mobile phase (100 114 Equol enantiomers were identified by HPLC using a Chiralcel OJ chiral phase column using the method shown in Example 2. The detection of equol was achieved by selected ion monitoring electrospray ionization mass spectrometry (ESI-MS). Mass chromatograms of a pure standard of S-equol, and of urine from an adult consuming soy food are shown in FIG. 4.

The retention index and mass chromatogram establish that it is exclusively the S-enantiomer of equol that is excreted in human urine as no detectable R-enantiomer of equol could be found. Analysis of the plasma from the same 'equol-producer' also revealed only the S-enantiomer of equol.

(b) Chemical Synthesis of Racemic Equol

Figure 5:
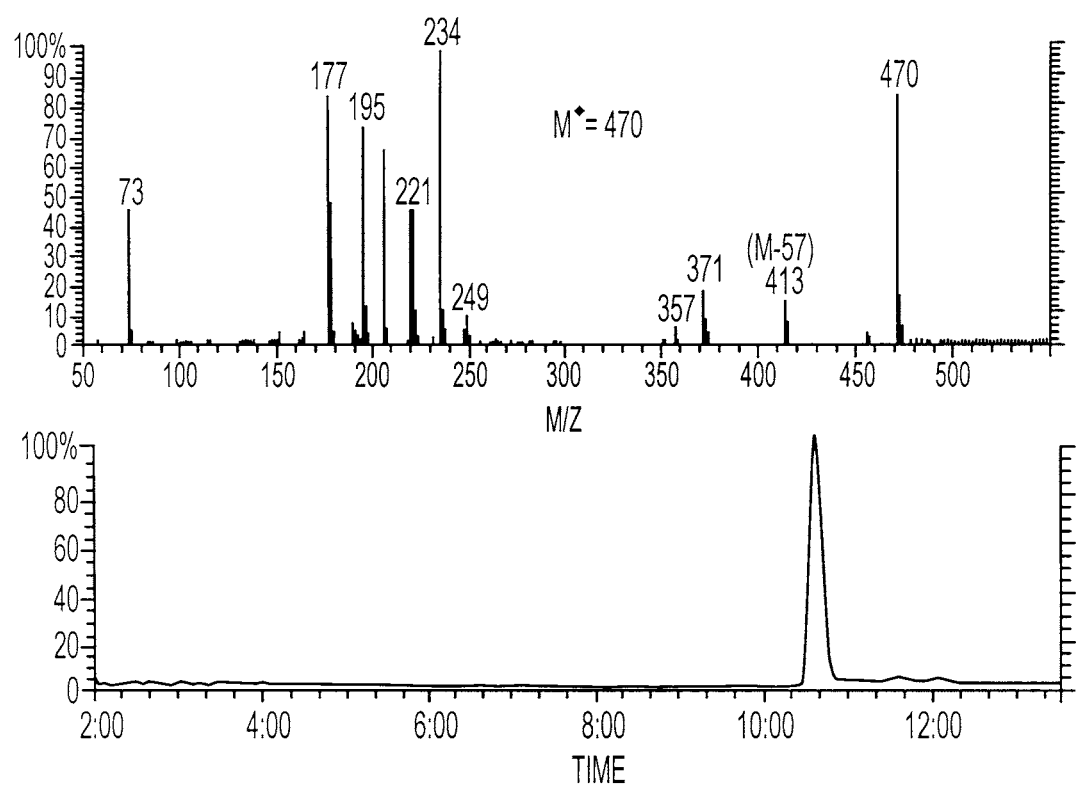
FIG. 5 shows a GC-MS analysis of the trimethylsilyl ether derivative of synthesized equol.

Daidzein (200 mg, 0.8 mmol) is dissolved in a mixture of glacial acetic acid (20 mL) and isopropanol (20 mL), and is reduced with 10% Pd on charcoal (150 mg) at 55 p.s.i.g. (3.7 atm gauge). At the end of the reaction (2 hours, TLC:isopropanol/n-hexane 1/4) the catalyst is filtered off, and the filtrate is evaporated. The crude residue is purified by chromatography on a silica gel column using as eluent a mixture of isopropanol and n-hexane (1:4 v/v), to give (±)equol as a pure product (160 mg, yield: 82%) crystallized from n-hexane. The product, colorless crystals, is not hygroscopic, is stable in air, and does not decompose during the final filtration procedure. The product of this chemical synthesis was in all respects identical with an authentic sample of (±)equol (racemic equol). FIG. 5 shows the GC-MS analysis of the trimethylsilyl ether derivative of synthesized product as a single pure peak and a mass spectrum that is consistent with the published electron ionization spectrum of the trimethylsilyl (TMS) ether derivative of authentic equol. The molecular ion as expected is at m/z 470 and the base peak at m/z 234. The purified equol product had a purity of greater than 99%, as confirmed by HPLC and mass spectrometry.

(c) Elution Order of S- and R-Enantiomer by Optical Dichroism

A racemic mixture of S-equol and R-equol were separated by chiral chromatography on a Chiralcel 0.1 Column using a flow-rate of 1.0 mL/min and with a gradient elution consisting of an initial mobile phase of 10% ethanol in hexane and increasing to 90% ethanol in hexane over a time period of 15 minutes according to the program shown in Table A:

TABLE A

| Time (min.) | % hexane | % ethanol |
| --- | --- | --- |
| 0 | 90 | 10 |
| 1.0 | 90 | 10 |
| 15.0 | 10 | 90 |
| 16.0 | 90 | 10 |
| 17.0 | 90 | 10 |

Figure 6:
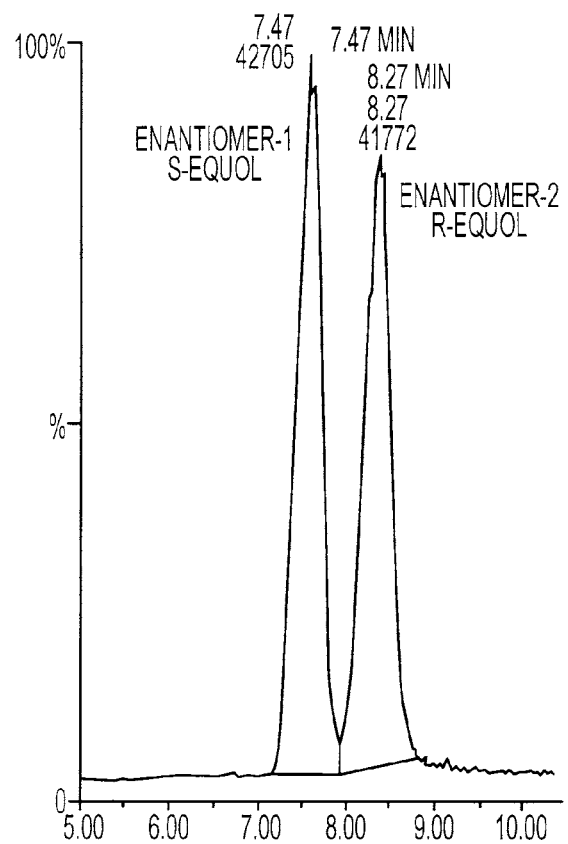
FIG. 6 shows another mass chromatogram of a chiral separation of S-equol and R-equol from a racemic mixture.

FIG. 6 shows the mass chromatogram of the ions recording (m/z 241) for a racemic mixture of S- and R-equol.

The first eluting material, designated as Enantiomer-1, and the second eluting material, designated as Enantiomer-2, were collected separately. Each enantiomer was weighed and the weighed samples dissolved in 1 mL of spectroscopic grade ethanol. Measurement of the optical rotation of each enantiomer was carried out at 20° C. using the light of wavelength in the line D of sodium.

Enantiomer-1 material (1.6 mg exact weight) had first and second measurements of −0.023 and −0.022, resulting in an optical rotation of −14 [−0.0225×1000/1.6], which corresponds with the S-enantiomer of equol. Enantiomer-2 material (1.7 mg exact weight) had first and second measurements of +0.023 and +0.023, resulting in an optical rotation of +13.5 [+0.023×1000/1.7], which corresponds with the R-enantiomer of equol.

(d) Production of S-Equol by Human Intestinal Bacteria

Freshly voided feces (1 g) from an equol-producer and a non-equol producer were separately incubated with 9 mL of sterile distilled water, trypticase soy broth and brain-heart infusion broth with the addition of daidzein (10 mg/L). The broths were incubated anerobically at 37° C. for 24 hr. The incubation mixtures were then centrifuged and the isoflavones isolated by passage through a Bond Elut C18 solid-phase cartridge (Varian Inc, Harbor City, Calif.), and eluted with methanol. The methanolic extract was then taken to dryness over nitrogen gas and re-dissolved in 100 µL mobile phase for analysis by high pressure liquid chromatography coupled with electrospray ionization mass spectrometry (ESI-MS).

The sample extracts (20 µL) were injected on column using the chiral phase column and elution properties described above in experiment (c). Detection of the two enantiomers was accomplished by selected ion recording in negative ion mode of the ion at m/z 241 specific for both equol enantiomers. The mass chromatograms of the incubation extracts were compared with a pure standard of the racemic equol that contained approximately equal proportions of S-equol and R-equol. Identification was based on the retention differences between the two enantiomers, where the S-equol enantiomer eluted before the R-equol enantiomer.

Figure 7:
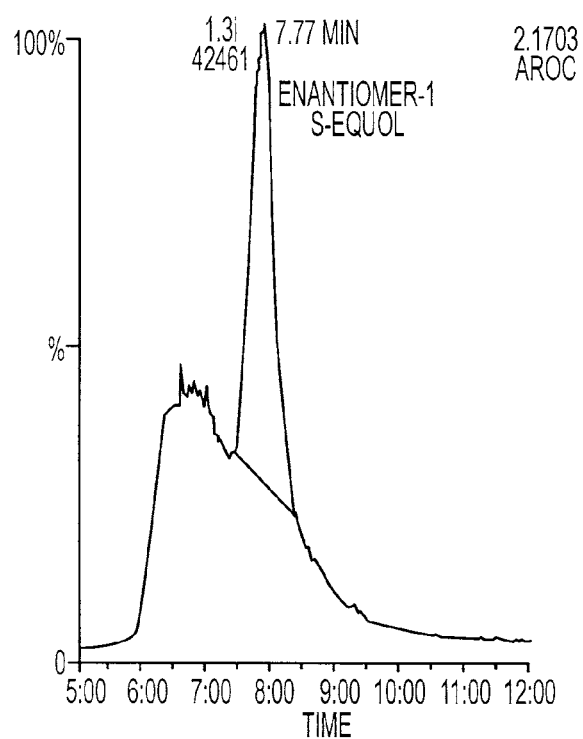
FIG. 7 shows a mass chromatogram of a chiral separation from an incubation product resulting from the bacterial conversion of daidzein by intestinal bacteria cultured from an 'equol-producer'.
Figure 8:
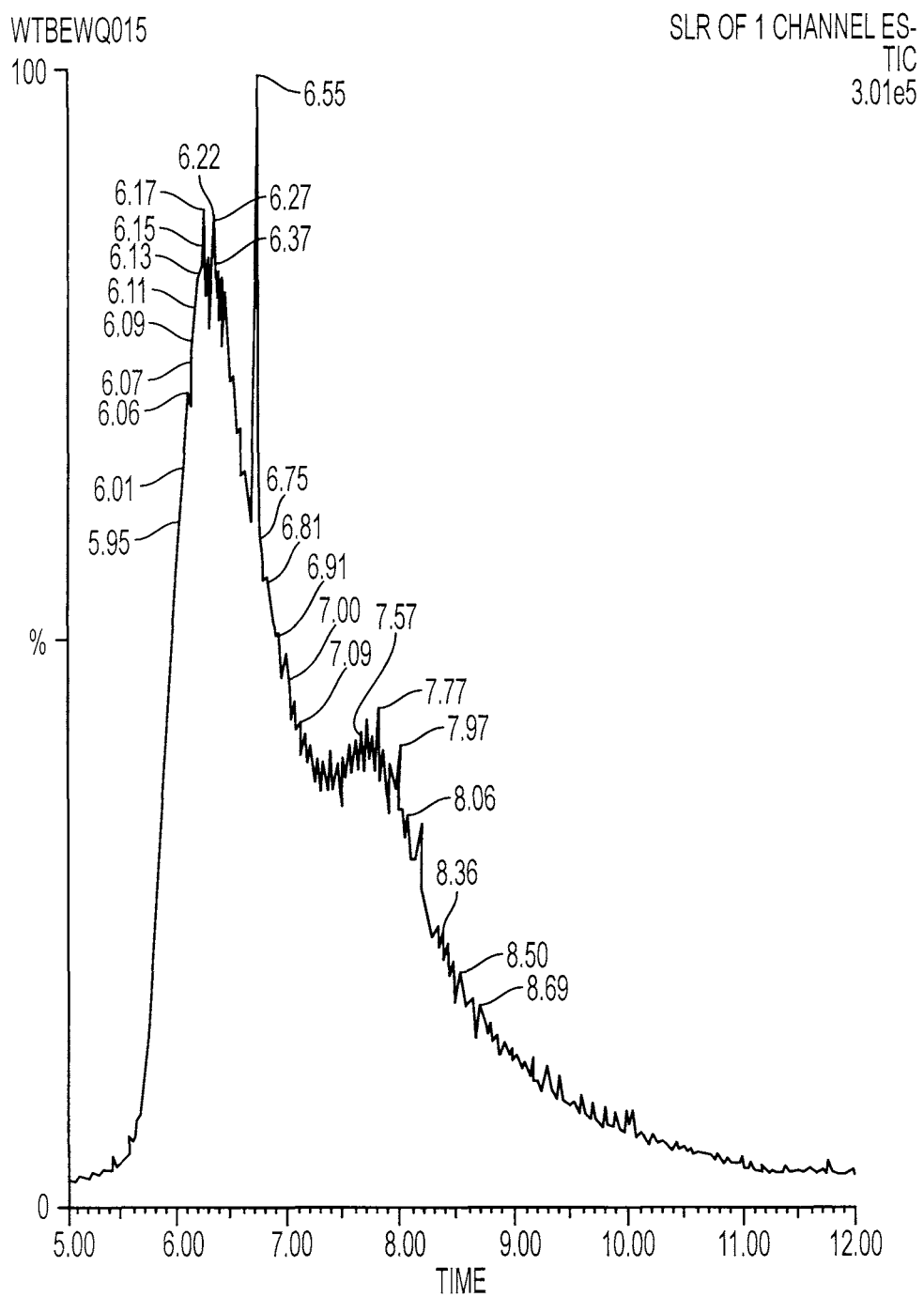
FIG. 8 shows a mass chromatogram of a chiral separation from an incubation product resulting from the bacterial conversion of daidzein by intestinal bacteria cultured from an 'non-equol-producer'.

FIG. 7 shows the mass chromatogram of the ions recording (m/z 241) for the incubation product resulting from the bacterial conversion of daidzein to equol by intestinal bacteria cultured from the 'equol-producer'. FIG. 7 shows a significant peak that corresponds to the S-equol enantiomer. By contrast, FIG. 8 shows the mass chromatogram of the ions recording (m/z 241) for the incubation product resulting from the bacterial conversion of daidzein to equol by intestinal bacteria cultured from the 'non-equol-producer', indicating that S-equol was detected in trivial or trace levels from its minor peak at the retention time corresponding to S-equol.

The product formed from intestinal bacterial conversion of daidzein to equol was a single peak (Enantiomer-1) corresponding to exclusively the S-equol enantiomer based upon ESI-MS analysis.

These studies confirm that human intestinal bacteria exclusively produce the S-equol enantiomer and this is consistent with the appearance of S-equol in human plasma and urine.

e) Determination of Receptor Binding Capacity of S- and R-Enantiomers

In vitro binding studies were performed to examine the relative affinities of S- and R-enantiomeric equol with the estrogen receptors ERα and ERβ.

Synthesis of Hormone Receptor Proteins: Full length rat ERα expression vector (pcDNA-ERα; RH Price UCSF) and ERβ expression vector (pcDNA-ERβ; TA Brown, Pfizer, Groton, Conn.) were used to synthesize hormone receptors in vitro using the TnT-coupled reticulocyte lysate system (Promega, Madison, Wis.) with T7-RNA polymerase, during a 90 min reaction at 30° C. Translation reaction mixtures were stored at −80° C. until further use.

Saturation isotherms: In order to calculate and establish the binding affinity of the S-equol and R-equol enantiomers for ERα and ERβ, 100 µL aliquots of reticulocyte lysate supernatant were incubated at optimal time and temperature; 90 min at room temperature (ERβ) and 18 hrs at 4° C. (ERα), with increasing (0.01-100 nm) concentrations of [$^3$H] 17β-estradiol ($E_2$). These times were determined empirically and represent optimal binding of receptor with estrogen. Nonspecific binding was assessed in a 300-fold excess of the ER agonist, diethylstilbestrol, in parallel tubes. Following incubation, bound and unbound [$^3$H]$E_2$ were separated by passing the incubation reaction through a 1 mL lipophilic Sephadex LH-20 (Sigma-Aldrich Co., Saint Louis, Mo.) column. Columns were constructed by packing a disposable pipette tip (1 mL; Labcraft, Curtin Matheson Scientific, Inc, Houston, Tex.) with TEGMD (10 mM Tris-Cl, 1.5 mM EDTA, 10% glycerol, 25 mM molybdate, and 1 mM dithiothreitol, pH 7.4)-saturated Sephadex according to previously published protocols (Handa et al., 1986; O'Keefe and Handa, 1990). For chromatography, the columns were re-equilibrated with TEGMD (100 µL), and the incubation reactions were added individually to each column and allowed to incubate on the column for an additional 30 min. Following this incubation, 600 µ, of TEGMD were added to each column, flow-through was collected, 4 mL scintillation fluid was added, and samples were counted (5 min each) in an 2900 TR Packard scintillation counter (Packard Bioscience, Meriden, Conn.).

Competition binding studies were used to assess the estrogenic properties of equol's S-equol and R-equol enantiomers. Based on the ability of S and R to compete with [$^3$H] $E_2$ for ER binding, the affinities for in vitro translated ER were shown to be very different for the two enantiomers. The S-equol enantiomer showed greatest affinity for ERβ [Kd (nM)=0.73±0.2], while its affinity for ERα was relatively low by comparison [$K_d$(nM)=6.41±1.0]. The R-equol enantiomer possessed a much lower affinity for both ERβ [Kd (nM)=15.4±1.3] and ERα [Kd (nM)=27.38±3.8]. For reference 17β-estradiol binds ERα with a Kd (nM)=0.13 and ERβ with a Kd (nM)= 0.15 in this system.

The study shows that only the S-equol enantiomer binds ER with sufficient affinity to have potential relevance to circulating equol levels reported in humans. Compared with 17β-estradiol the relative binding affinities of the S-equol and R-equol enantiomers for ERα were 49-fold and 211-fold less, respectively. However, the S-equol enantiomer seems to be largely ERβ-selective with a relatively high affinity for ERβ, while the R-equol enantiomer binds with approximately 100-fold less affinity. The separate and associated determination that exclusively S-equol is found in human plasma and urine is significant in view of the specificity in binding of the two enantiomers.

EXAMPLES

Example 1

Separation of Racemic Equol into Separate Enantiomers by HPLC

Figure 9:
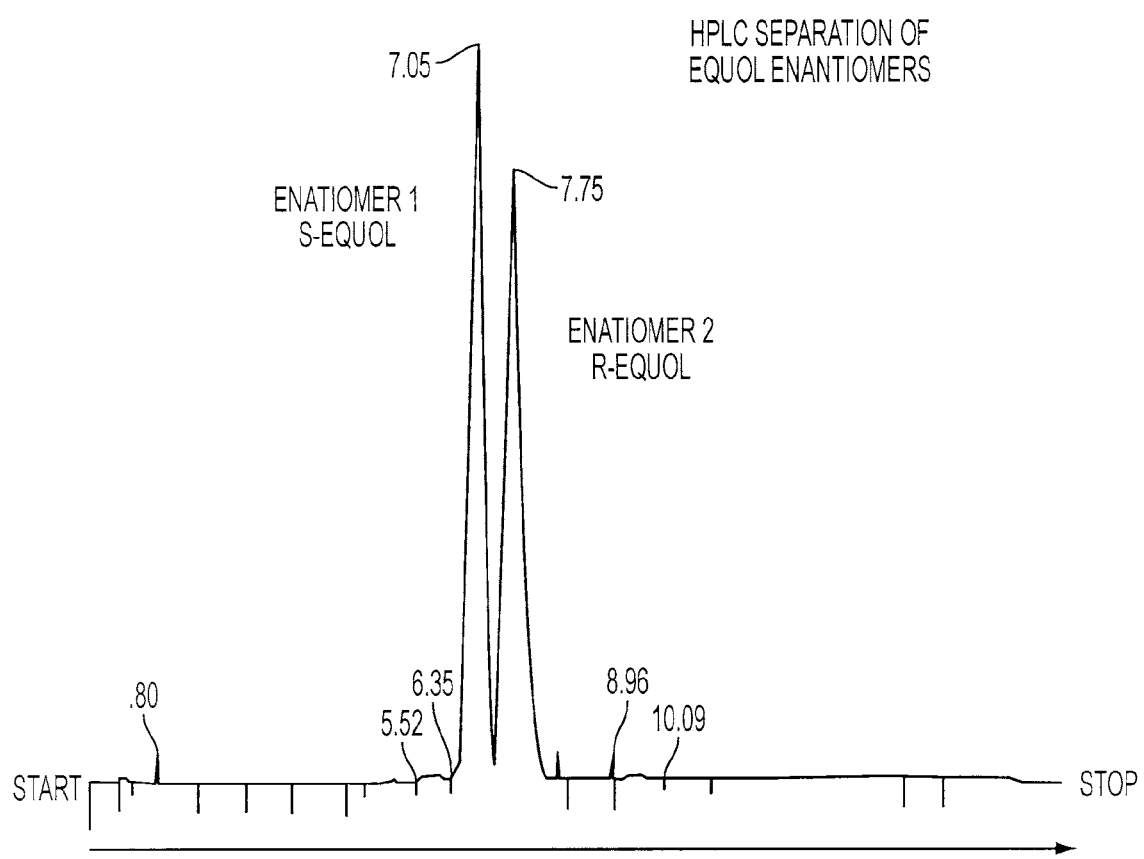
FIG. 9 shows the separation and elution of the equol enantiomers from a chiral-phase column.

A synthetic racemic mixture of S- and R-equol was prepared in accordance with the chemical synthesis described in experiment (b) in the Experiments section, and was passed through a Chiralcel OJ (0.46 cm diameter×25 cm long), supplied by Daicel Chemical Industries Ltd. The column uses cellulose tris(4-methylbenzoate) on a 10 μm silica-gel substrate. The mobile phase used was a gradient elution beginning with hexane 90%/ethanol 10% and linearly increasing to a final composition of hexane 10%/ethanol 90% over a 15 min period according to Table A at a flow-rate of 1 milliliters per minute (mL/min). The elution of equol from the column was detected by UV absorbance at 260 nm. FIG. 9 shows the elution of equol enantiomers using the chiral-phase column. R-equol enantiomer had a residence time of 7.05 min., while the S-equol enantiomer had a residence time of 7.75 min. The identification of the enantiomers was confirmed from their retention indices and comparison against pure enantiomeric standards that had been characterized by optical dichroism.

Example 2

Absorption and Bioavailability of Equol

Figure 10:
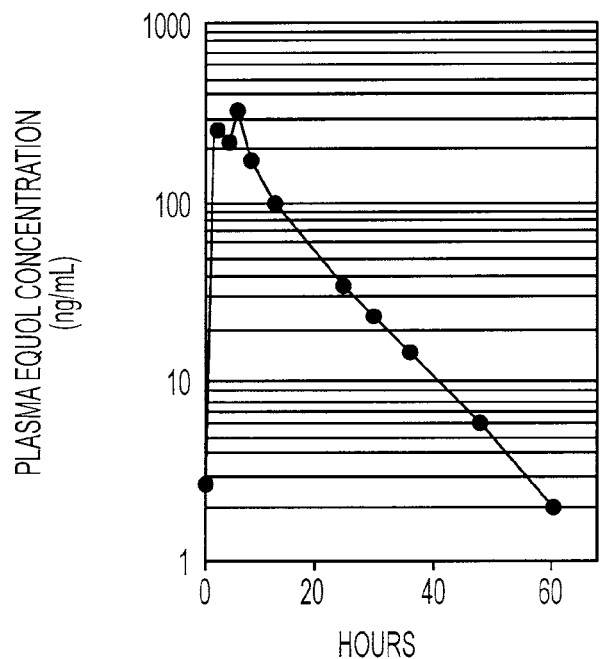
FIG. 10 shows the plasma appearance/disappearance curve for (±)equol in a healthy adult female after oral administration.

A healthy adult human female subject was administered a single bolus oral 25-mg dose of equol, and blood plasma levels of equol are monitored. Absorption through the intestinal tract proceeded rapidly, attaining a maximal plasma concentration after 4-6 hr, and thereafter disappearing from the circulation with a terminal elimination half-life of 8.8 hr. The pharmacokinetics of ±equol, shown in Table B, are similar to those of other isoflavones, although showing a slower plasma clearance (Cl/F=6.85 L/h) compared with its precursor, daidzein (Cl/F=17.5 L/h), and showing a relatively high dose adjusted bioavailability (AUC inf/F=145.8 ng/Ml/hr/mg equol). FIG. 10 shows the plasma appearance/disappearance curve for (±)equol expressed as log/linear plot depicting equol's pharmacokinetics in the healthy adult female after oral administration of (±)equol. Table B also shows comparative values previously published for daidzein in healthy women.

TABLE B

| Adult Female | Equol | Daidzein |
| --- | --- | --- |
| t½ (h) | 8.76 | 9.34 |
| Vd/F (L) | 86.7 | 236.4 |
| Cl/F (L/h) | 6.85 | 17.5 |
| $AUC_{inf}$(ng/Ml/hr) | 3646 | 1470 |

Example 3

Estrogenic Activity of Equol

Figure 11:
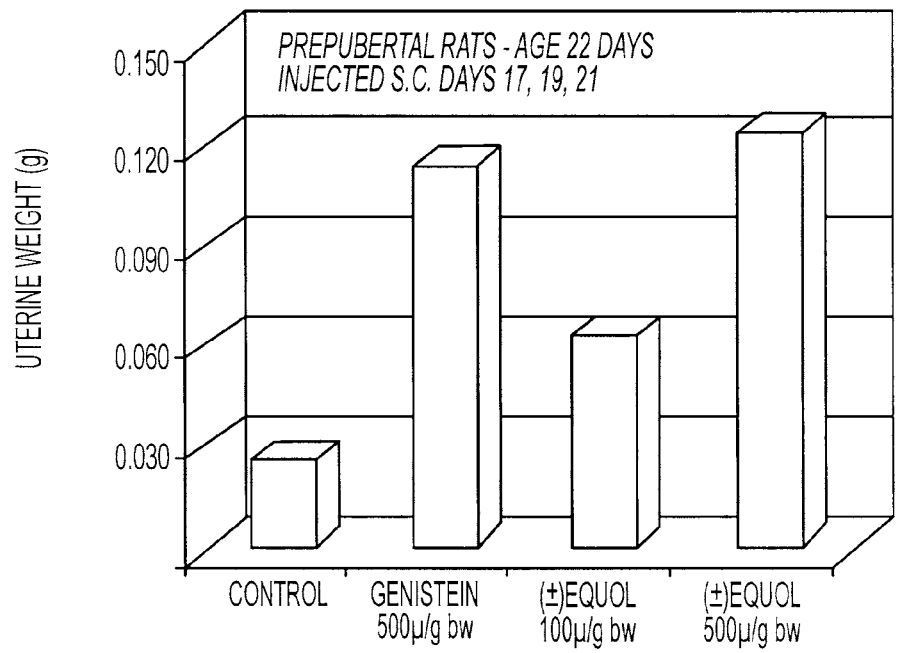
FIG. 11 shows estrogenic activity of genistein and (±)equol on the uterus of immature rats.

A racemic mixture of a chemically-synthesized equol was sub-cutaneously injected (both 100 mg and 500 mg doses) into prepubertal 22-day old Sprague-Dawley rats to compare its estrogenic activity on the uterus of immature rats. Also tested were genistein (500 mg dose) and DMSO (control). Uterine weights were measured on days 17, 19, and 21. FIG. 11 shows that the racemic equol was more than twice as estrogenic than genistein in this model when allowing for the fact that half of the injected dose is the inactive R-equol enantiomer.

Example 4

Bacterial Conversion of Glucoside to Aglycon Forms in Soy Foods

The first step in the conversion of daidzein to equol in foods is the conversion of the glucoside form of the isoflavone to the aglycon form in preparation for the enzymic reduction of the aglycon to equol. A large number of organisms were tested for their ability to achieve the conversion. Sterile soy beverage containing approximately 3.5% protein, 8% carbohydrate and daidzin at approximately 16 mg/L was inoculated with a test organism and incubated at a suitable temperature. Incubation temperatures in the range of 20° to 40° C. were considered suitable and, for most of the organisms tested, a temperature of 30° or 37° was preferred. Incubation was carried out under anaerobic conditions in the majority of the bacterial strains. The progress of the conversion of daidzin to daidzein was followed by analyzing samples for unreacted daidzein, taken at intervals from 10 hours up to 72 hour after incubation commenced. The results are shown in Table C. Of fifty four species/strains of bacteria tested, there were 26 which were unable to convert daidzin to daidzein. Of the 28 organisms that were able to convert daidzin to daidzein, four were able to do the conversion rapidly, taking from 10 hours to 24 hour to achieve virtually 100% conversion. There were twelve types that converted at a medium rate, taking from 25 to 72 hours to achieve virtually complete conversion. The remaining organisms that provided conversion were slow, with less than 50% conversion being completed within the 72 hour incubation period. The organisms showing rapid conversion included *Enterococcus faecalis*, a *Lactobacillus plantarum, Listeria welshimeri*, and a mixed culture of organisms isolated from equine feces Of seven *Lactobacillus plantarum* strains tested, one was fast, four classified as medium and two were slow convertors. Other organisms able to convert efficiently the glucoside to the aglycon included *Bacteriodes fragilis, Bifidobacterium lactis, Eubactria limosum, Lactobacillus casei, lactobacillus acidophilous, Lactobacillus delbruekii, Lactobacillus paracasei, Listeria monocytogenes, Micrococcus luteus, Proprionobacterium fi-eudenreichii* and *Sacharomyced boulardii*.

TABLE C

Rate of Conversion of Daidzin to Daidzein
by Various Microorganisms in a Food Base
(Incubation at 37° C. under Anaerobic Conditions)

| Bacterial species/strain | Time to reach 50% conversion (hours) | Time to reach >90% conversion (hours) |
|---|---|---|
| Bacteroides fragilis | 64 | ND |
| Bifidobacterium lactis Bb-12 (ChB) | 25 | >40 |
| Bifidobacterium lactis STSC 380 (lafti) | 40 | ND |
| Enterococcus faecalis STSC 030 | 5 | 8 |
| Eubacterium limosum | 35 | >64 |
| Mixed culture from equine feces | 8 | 15 |
| Lactobacillus acidophilus STSC 220 (GbA) | 25 | 40 |
| Lactobacillus acidophilus STSC 375 | 28 | 64 |
| Lactobacillus casei STSC 175 | 25 | 40 |
| Lactobacillus casei STSC 330 | 30 | 64 |
| Lactobacillus casei STSC 355 | 25 | 64 |
| Lactobacillus delbruekii STSC 350 | 40 | ND |
| Lactobacillus paracasei STSC 385 | 22 | 48 |
| Lactobacillus paracasei STSC 345 | 30 | 48 |
| Lactobacillus paracasei ChC | 17 | 25 |
| Lactobacillus plantarum STSC 300 Lp 429 | 16 | 24 |
| Lactobacillus plantarum Lp 2904 | 27 | >30 |
| Lactobacillus plantarum Lp 1572 | 27 | >30 |
| Lactobacillus plantarum STSC 325 | 48 | ND |
| Lactobacillus plantarum STSC 335 | 64 | ND |
| Lactobacillus plantarum Lp 7376 | 25 | 60 |
| Lactobacillus plantarum Lp 704 | 27 | 40 |
| Listeria monocytogenes STSC 135 | 27 | 40 |
| Listeria welshimeri STSC 260 | 15 | 24 |
| Micrococcus luteus STSC 370 | 50 | ND |
| Mixed culture containing: Bifidobacterium lactis, Lactobacillus acidophilus, Lactococcus lactis, Enterococcus faecium, Lactobacillus casei and Lactobacillus salivarius. | 18 | 32 |
| Propionibacterium freudenreichii | 18 | 22 |
| Saccharomyces boulardii ATCC 74012 | 64 | ND |

'ND' - Unable to estimate time
'>' values were approaching the category threshold, but incubation ceased before threshold was reached.

Example 5

Bacterial Conversion of Daidzein to Equol in Food

In an experiment to discover bacteria, or combinations of bacteria, that can metabolise daidzein in a reducing environment, samples of a daidzein-enriched soy milk containing approximately 20 mg/L of daidzein were inoculated with different bacteria either in pure culture or as a combination of several organisms. The inoculated soy milks were incubated anaerobically at 37° C. for up to 42 hours Samples were withdrawn at intervals throughout the time period of the experiment and analyzed for isoflavone content, in particular the daidzein content. Conversion of daidzein to equol would be accompanied by lowering of the level of daidzein in the product over time, with the hydrogenated product, equol, taking its place. No significant changes in isoflavone content, outside of the daidzein level, were found in any of the inoculated products, which effectively demonstrates the stability of isoflavones (including daidzein when suitable metabolizing bacteria are absent or inactive). The results are shown in Table D. Of seven different innocula studied, four showed no change in daidzein content during the full incubation period. Three of the inoculated samples demonstrated substantial lowering of the level of daidzein with corresponding conversion to the hydrogenated compound. The organisms effecting this change were *Proprionobacteria freundenreichii*, a mixed culture containing. *Bifidobacterium lactis, Lactobacillus acidophilus, Lactococcus lactis, Enterococcus faecium, Lactobacillus casei* and *Lactobacillus salivarius*; and a mixed culture isolated from equine feces. Daidzein loss to approximately 50% of the initial level occurred in less than 15 hours with the equine feces mixed culture and took up to 25 hours with the other two cultures

TABLE D

Conversion of Daidzein During Growth of
Various Microorganisms in a Food Base
(Incubation at 37° C. under Anaerobic Conditions)

| Bacterial species/strain | Time required to metabolize 50% of the daidzein present |
|---|---|
| Uninoculated Food medium | Not metabolized |
| Propionobacterium acnes | Not metabolized |
| Propionobacterium freundenreichii | 25 hours |
| Lactobacillus fermentum | Not metabolized |
| Mixed culture from equine feces | 15 hours |
| Mixed culture containing: Bifidobacterium lactis, Lactobacillus acidophilus, Lactococcus lactis, Enterococcus faecium, Lactobacillus casei and Lactobacillus salivarius | 25 hours |
| Lactobacillus salivarius | Not metabolized |
| Bacterioides vulgatus | Not metabolized |

Example 6

Bacterial Production of S-Equol in a Food Product

A simple, light broth was prepared containing hydrolyzed plant and milk proteins with salt and sugar. Daidzein, at a level of approximately 2 mg/L, was added to the broth. The broth was cooked in a pressure cooker for about 15 minutes and after cooling to room temperature was inoculated with a mixed culture of organisms derived from the gastrointestinal tract of a person known to produce equol when consuming soy milk as part of a regular diet. The broth was held at a temperature of 37° C. for 24 hours and then analyzed. The live organisms can then optionally be destroyed by a method commonly used to deactivate organisms in a food product. The presence of equol (presumed to be S-equol) derived from the daidzein was confirmed by electrospray mass spectrometry of an extract of the broth.

Example 7

Enzymatic Production of S-Equol in a Food Product

A mixed culture of bacteria, containing *Bifidobacterium lactis, Lactobacillus acidophilus, Lactococcus lactis, Enterococcus faecium, Lactobacillus casei* and *Lactobacillus salivarius*, is cultured in a nutritive tryptone broth anaerobically at 37° C. for from about 24 hours to 36 hours. The bacteria are separated from the culture broth by centrifugation at about 10,000 gravities of force, and the cells are suspended in about 0.9% saline solution, and then are re-centrifuged. The washed, separated cells are used to prepare an extract of active enzymes using techniques well know to those practicing in the art of enzymology and biochemistry. The crude enzyme mixture can be used as is, or can be further purified by conventional enzyme preparation techniques into a purified enzyme extract.

The purified enzyme mixture is added to a food product that contains 10 mg/L daidzein. The composition is incubated for about 2 hours at a temperature of about 30° C. to 40° C. while maintaining mild anaerobic conditions. The enzymes are then inactivated by heating the composition to about 95° to 100° C., resulting in a food product containing S-equol.

What is claimed:

1. A food composition consisting essentially of a food component and an active agent, wherein the active agent consists essentially of S-equol having an enantiomeric purity of 90% minimum enantiomeric excess (EE) and is essentially free of daidzein and genistein, and wherein the S-equol is present in an amount sufficient to achieve a health benefit in a mammal.

2. The food composition of claim 1, wherein the food composition comprises, per serving of food, from about 1 mg to about 300 mg, S-equol.

3. The food composition of claim 2, wherein the food composition comprises, per serving of food, from about 10 mg to about 200 mg, S-equol.

4. The food composition of claim 1, wherein the S-equol is conjugated at the C-4' or C-7 position to form a conjugate selected from the group consisting of glucuronide, sulfate, acetate, propionate, glucoside, acetyl-glucoside, malonyl-glucoside, and mixtures thereof.

5. The food composition of claim 1, wherein the food composition comprises a probiotic food, a prebiotic food, or a dietary food product.

6. The food composition of claim 1, wherein the food composition is a beverage.

7. The food composition of claim 1 wherein the S-equol has an enantiomeric purity of 96% minimum EE.

8. The food composition of claim 7 wherein the S-equol has an enantiomeric purity of 98% minimum EE.

9. The food composition of claim 1, wherein the mammal is a human.

10. The food composition of claim 1, wherein the S-equol is present in an amount sufficient to produce a transient level of S-equol in the blood plasma of the mammal of at least 5 ng/mL.

11. The food composition of claim 10, wherein the S-equol is present in an amount sufficient to produce a transient level of S-equol in the blood plasma of the mammal of at least 10 ng/mL.

12. The food composition of claim 1, wherein the S-equol is present in an amount sufficient to produce a transient level of S-equol in the urine of the mammal of at least 1000 nmol/L.

13. The food composition of claim 1, wherein the mammal is a human.

14. The food composition of claim 1, wherein the S-equol is present in an amount sufficient to produce a transient level of S-equol in the blood plasma of the mammal of at least 5 ng/mL.

15. The food composition of claim 1, wherein the S-equol is present in an amount sufficient to produce a transient level of S-equol in the blood plasma of the mammal of at least 10 ng/mL.

16. The food composition of claim 1, wherein the S-equol is present in an amount sufficient to produce a transient level of S-equol in the urine of the mammal of at least 1000 nmol/L.

17. An orally consumable composition consisting essentially of S-equol as an active agent and an adjuvant, carrier, diluent, filler, excipient and/or food component, wherein the S-equol has an enantiomeric purity of 90% minimum enantiomeric excess (EE) and is essentially free of daidzein and genistein, and wherein the S-equol is present in an amount sufficient to achieve a health benefit in a mammal.

18. The orally consumable composition of claim 17, wherein the mammal is a human.

19. The orally consumable composition of claim 17, wherein the S-equol has an enantiomeric purity of 96% minimum enantiomeric excess (EE).

20. The orally consumable composition of claim 19, wherein the S-equol has an enantiomeric purity of 98% minimum enantiomeric excess (EE).

21. The orally consumable composition of claim 17, wherein the S-equol is present in an amount sufficient to produce a transient level of S-equol in the blood plasma of the mammal of at least 5 ng/mL.

22. The orally consumable composition of claim 21, wherein the S-equol is present in an amount sufficient to produce a transient level of S-equol in the blood plasma of the mammal of at least 10 ng/mL.

23. The orally consumable composition of claim 17, wherein the S-equol is present in an amount sufficient to produce a transient level of S-equol in the urine of the mammal of at least 1000 nmol/L.

24. The orally consumable composition of claim 17, wherein the composition is a food product or a dietary supplement.

25. A food composition or dietary supplement consisting essentially of an active agent consisting of S-equol, and an adjuvant, carrier, diluent, filler, excipient and/or food component, wherein the S-equol has an enantiomeric purity of 90% minimum enantiomeric excess (EE) and is essentially free of daidzein and genistein, and wherein the S-equol is present in an amount sufficient to achieve a health benefit in a mammal.

26. The orally consumable composition of claim 17, wherein the composition is formulated as a unit dose.

27. The orally consumable composition of claim 26, wherein the unit dose is selected from the group consisting of a tablet, a capsule, a lozenge, and a cachet.

28. An orally consumable composition consisting essentially of equol and an adjuvant, carrier, diluent, filler, excipient and/or food component, wherein the equol is present as a non-racemic mixture having an excess of the S-enantiomer of equol (S-equol), wherein the S-equol has an enantiomeric purity of 90% minimum enantiomeric excess (EE) and is essentially free of daidzein and genistein, and wherein the S-equol is present in an amount sufficient to achieve a health benefit in a mammal.

29. The orally consumable composition of claim 28, wherein the S-equol has an enantiomeric purity of 96% minimum enantiomeric excess (EE).

30. The orally consumable composition of claim 29, wherein the S-equol has an enantiomeric purity of 98% minimum enantiomeric excess (EE).

31. The orally consumable composition of claim 28, wherein the composition is a food product or a dietary supplement.

32. The orally consumable composition of claim 28, wherein the composition is formulated as a unit dose.

33. The orally consumable composition of claim 32, wherein the unit dose is selected from the group consisting of a tablet, a capsule, a lozenge, and a cachet.

34. The orally consumable composition of claim 28, wherein the mammal is a human.

35. The orally consumable composition of claim 28, wherein the S-equol is present in an amount sufficient to produce a transient level of S-equol in the blood plasma of the mammal of at least 5 ng/mL.

36. The orally consumable composition of claim 28, wherein the S-equol is present in an amount sufficient to produce a transient level of S-equol in the blood plasma of the mammal of at least 10 ng/mL.

37. The orally consumable composition of claim 28, wherein the S-equol is present in an amount sufficient to produce a transient level of S-equol in the urine of the mammal of at least 1000 nmol/L.

* * * * *